(12) United States Patent
Brown et al.

(10) Patent No.: US 8,791,084 B2
(45) Date of Patent: Jul. 29, 2014

(54) INHIBITION OF SOX9 FUNCTION IN THE TREATMENT OF PROTEOGLYCAN-ASSOCIATED PATHOPHYSIOLOGICAL CONDITIONS

(75) Inventors: Arthur Brown, London (CA); Paul Gris, Chapel Hill, NC (US)

(73) Assignee: Robarts Research Institute, London, Ontario (CA)

( * ) Notice: Subject to any disclaimer, the term of this patent is extended or adjusted under 35 U.S.C. 154(b) by 351 days.

(21) Appl. No.: 12/447,238

(22) PCT Filed: Oct. 25, 2007

(86) PCT No.: PCT/CA2007/001902
§ 371 (c)(1),
(2), (4) Date: Apr. 24, 2009

(87) PCT Pub. No.: WO2008/049226
PCT Pub. Date: May 2, 2008

(65) Prior Publication Data
US 2010/0028364 A1    Feb. 4, 2010

Related U.S. Application Data

(60) Provisional application No. 60/863,202, filed on Oct. 27, 2006.

(51) Int. Cl.
*A61K 48/00* (2006.01)
(52) U.S. Cl.
USPC .......................................................... 514/44
(58) Field of Classification Search
None
See application file for complete search history.

(56) References Cited

FOREIGN PATENT DOCUMENTS

| WO | WO 2003102130 A2 | 12/2003 |
|---|---|---|
| WO | WO 2005100552 A2 | 10/2005 |
| WO | WO 2008049226 A1 | 5/2008 |

OTHER PUBLICATIONS

Zehentner et al. (Develop. Growth Differ. 2002).*
Buss et al. Brain 2007, vol. 130:940-953.*
Bradbury, EJ., et al., "Chondroitinase ABC promotes functional recovery after spinal cord injury." Nature 416 (6881):636-40.
Costa, S., et al., "Astroglial Permissivity for Neuritic Outgrowth in Neuron-Astrocyte Cocultures Depends on Regulation of Laminin Bioavailability". GLIA 37:105-113 (2002).
Fok-Seang, J., et al., "An analysis of astrocytic cell lines with different abilities to promote axon growth." Brain Research 689 (1995) 207-223.
Grimpe, B., et al., "A NovelDNAEnzyme Reduces Glycosaminoglycan Chains in the Glial Scar and Allows Microtransplanted Dorsal Root Ganglia Axons to Regenerate beyond Lesions in the Spinal Cord." The Journal of Neuroscience, Feb. 11, 2004 • 24(6):1393-1397.
Gris, P., et al., "Transcriptional Regulation of Scar Gene Expression in Primary Astrocytes." GLIA 55:1145-1155 (2007).
Gris, P., et al., "Gene expression profiling in anti-CD11d mAb-treated spinal cord-injured rats." Journal of Neuroimmunology 209 (2009) 104-113.
Logan, A., et al., "Inhibition of glial scarring in the injured rat brain by a recombinant human monoclonal antibody to transforming growth factor-b2." European Journal of Neuroscience, vol. 11, pp. 2367±2374, 1999.
McKeon RJ et al., "Reduction of Neurite Outgrowth in a Model of Glial Scarring following CNS Injury is Correlated with the Expression of Inhibitory Molecules on Reactive Astrocytes." The Journal of Neuroscience, Nov. 1991, (11): 3398-3411.
McKeon RJ et al., "The Chondroitin Sulfate Proteoglycans Neurocan and Phosphacan are Expressed by Reactive Astrocytes in the Chronic CNS Glial Scar". The Journal of Neuroscience, Dec. 15, 1999, 19(24):10778-10788.
Tom, VJ., et al., "Astrocyte-Associated Fibronectin is Critical for Axonal Regeneration in Adult White Matter." The Journal of Neuroscience, Oct. 20, 2004 • 24(42):9282-9290.
Wiksten, M., et al., "Regeneration of Adult Rat Spinal Cord is Promoted by the Soluble KDI Domain of gamma1 Laminin." Journal of Neuroscience Research 78:403-410 (2004).
Zuo, J., et al., "Degradation of Chondroitin Sulfate Proteoglycan Enhances the Neurite-Promoting Potential of Spinal Cord Tissue." Experimental Neurology 154,654-662 (1998).
Sumi, E. et al., "SRY-RElated HMG Box 9 Regulates the Expression of Col4a2 Through Transactivating ITs Enhancer Element in Mesangial Cells." Am. J. Pathol., Jun. 2007, vol. 170, pp. 1854-1864.
International Search Report based on International Application No. PCT/CA2007/001902 (Jan. 14, 2008).
Wegner, M., et al., "From Stem Cells to Neurons and Glia: a Soxist's View of Neural Development." Trends in Neuroscience 28 (11):583-88 (2005).

* cited by examiner

*Primary Examiner* — Kimberly Chong
(74) *Attorney, Agent, or Firm* — Cooley LLP

(57) ABSTRACT

A method of treating a pathophysiological condition caused by the production of growth-inhibiting proteoglycans is provided. It is based on the finding that down-regulation of SOX9 results in decreased production of growth-inhibiting factors such as proteoglycans, and increased production of growth-promoting factors such as a laminin and fibronectin. The method of the present invention comprises the inhibition of SOX9 expression and function with an inhibitor such as an antisense oligonucleotide or a siRNA.

6 Claims, 11 Drawing Sheets

Hum SOX9 - SEQ ID NO: 1    Mus SOX9 - SEQ ID NO: 2

```
Hum SOX9    1  MNLLDPFMKMTDEQEKGLSGAPSPTMSEDSAGSPCPSGSGSDTENTRPQENTFPKGEPDL   60
               MNLLDPFMKMTDEQEKGLSGAPSPTMSEDSAGSPCPSGSGSDTENTRPQENTFPKGEPDL
Mus SOX9    1  MNLLDPFMKMTDEQEKGLSGAPSPTMSEDSAGSPCPSGSGSDTENTRPQENTFPKGEPDL   60

Hum SOX9   61  KKESEEDKFPVCIREAVSQVLKGYDWTLVPMPVRVNGSSKNKPHVKRPMNAFMVWAQAAR  120
               K+ESEEDKFPVCIREAVSQVLKGYDWTLVPMPVRVNGSSKNKPHVKRPMNAFMVWAQAAR
Mus SOX9   61  KRESEEDKFPVCIREAVSQVLKGYDWTLVPMPVRVNGSSKNKPHVKRPMNAFMVWAQAAR  120

Hum SOX9  121  RKLADQYPHLHNAELSKTLGKLWRLLNESEKRPFVEEAERLRVQHKKDHPDYKYQPRRRK  180
               RKLADQYPHLHNAELSKTLGKLWRLLNESEKRPFVEEAERLRVQHKKDHPDYKYQPRRRK
Mus SOX9  121  RKLADQYPHLHNAELSKTLGKLWRLLNESEKRPFVEEAERLRVQHKKDHPDYKYQPRRRK  180

Hum SOX9  181  SVKNGQAEAEEEATEQTHISPNAIFKALQADSPHSSSGMSEVHSPGEHSGQSQGPPTPPTT  240
               SVKNGQAEAEEEATEQTHISPNAIFKALQADSPHSSSGMSEVHSPGEHSGQSQGPPTPPTT
Mus SOX9  181  SVKNGQAEAEEEATEQTHISPNAIFKALQADSPHSSSGMSEVHSPGEHSGQSQGPPTPPTT  240

Hum SOX9  241  PKTDVQPGKADLKREGRPLPEGGRQPPIDFRDVDIGELSSDVISNIETFDVNEFDQYLPP  300
               PKTDVQ GK DLKPEGRPL EGGRQPPIDFRDVDIGELSSDVISNIETFDVNEFDQYLPP
Mus SOX9  241  PKTDVQAGKVDLKREGRPLAEGGRQPPIDFRDVDIGELSSDVISNIETFDVNEFDQYLPP  300

Hum SOX9  301  NGHPGVPATHGQVTYTGSYGISSTAATPASAGHVWMSKQQAPPPPPQQPPQAPPAPQAPP  360
               NGHPGVPATHGQVTYTGSYGISSTA TPA+AGHVWMSKQQA   PPP
Mus SOX9  301  NGHPGVPATHGQVTYTGSYGISSTAPTPATAGHVWMSKQQA--PPPPPQQPPQAPQAPQA  358

Hum SOX9  361  QPQAAPPQQPAAPPQQPQAHTLTTLSSEPGQSQRTHIKTEQLSPSHYSEQQQHSPQQIAY  420
                 PQ   P Q    PQQ QAHTLTTLSSEPGQSQRTHIKTEQLSPSHYSEQQQHSPQQI+Y
Mus SOX9  359  PPQQQAPPQQPQAPQQQQAHTLTTLSSEPGQSQRTHIKTEQLSPSHYSEQQQHSPQQISY  418

Hum SOX9  421  SPFNLPHYSPSYPPITRSQYDYTDHQNSSSYYSHAAGQGTGLYSTFTYMNPAQRPMYTPI  480
               SPFNLPHYSPSYPPITRSQYDY DHQNS SYYSHAAGQG+GLYSTFTYMNPAQRPMYTPI
Mus SOX9  419  SPFNLPHYSPSYPPITRSQYDYADHQNSGSYYSHAAGQGSGLYSTFTYMNPAQRPMYTPI  478

Hum SOX9  481  ADTSGVPSIPQTHSPQHWEQPVYTQLTRP  509
               ADTSGVPSIPQTHSPQHWEQPVYTQLTRP
Mus SOX9  479  ADTSGVPSIPQTHSPQHWEQPVYTQLTRP  507
```

Figure 9(A)

```
         Hum SOX9 - SEQ ID NO: 1    Rat SOX9 - SEQ ID NO: 3

Hum SOX9    1   MNLLDPFMKMTDEQEKGLSGAPSPTMSEDSAGSPCPSGSGSDTENTRPQENTFPKGEPDL   60
                MNLLDPFMKMTDEQEKGLSGAPSPTMSEDSAGSPCPSGSGSDTENTRPQENTFPKGEPDL
Rat SOX9    1   MNLLDPFMKMTDEQEKGLSGAPSPTMSEDSAGSPCPSGSGSDTENTRPQENTFPKGEPDL   60

Hum SOX9   61   KKESEEDKFPVCIREAVSQVLKGYDWTLVPMPVRVNGSSKNKPHVKRPMNAFMVWAQAAR  120
                KKESEEDKFPVCIREAVSQVLKGYDWTLVPMPVRVNGSSKNKPHVKRPMNAFMVWAQAAR
Rat SOX9   61   KKESEEDKFPVCIREAVSQVLKGYDWTLVPMPVRVNGSSKNKPHVKRPMNAFMVWAQAAR  120

Hum SOX9  121   RKLADQYPHLHNAELSKTLGKLWRLLNESEKRPFVEEAERLRVQHKKDHPDYKYQPRRRK  180
                RKLADQYPHLHNAELSKTLGKLWRLLNESEKRPFVEEAERLRVQHKKDHPDYKYQPRRRK
Rat SOX9  121   RKLADQYPHLHNAELSKTLGKLWRLLNESEKRPFVEEAERLRVQHKKDHPDYKYQPRRRK  180

Hum SOX9  181   SVKNGQAEAEEATEQTHISPNAIFKALQADSPHSSSGMSEVHSPGEHSGQSQGPPTPPTT  240
                SVKNGQAEAEEATEQTHISPNAIFKALQADSPHSSSGMSEVHSPGEHSGQSQGPPTPPTT
Rat SOX9  181   SVKNGQAEAEEATEQTHISPNAIFKALQADSPHSSSGMSEVHSPGEHSGQSQGPPTPPTT  240

Hum SOX9  241   PKTDVQPGKADLKREGRPLPEGGRQPPIDFRDVDIGELSSDVISNIETFDVNEFDQYLPP  300
                PKTDVQ GK DLKREGRPL EGGRQPPIDFRDVDIGELSSDVISNIETFDVNEFDQYLPP
Rat SOX9  241   PKTDVQAGKVDLKREGRPLAEGGRQPPIDFRDVDIGELSSDVISNIETFDVNEFDQYLPP  300

Hum SOX9  301   NGHPGVPATHGQVTYTGSYGISSTAATPASAGHVWMSKQQAPPPPPQQPPQAPPAPQAPP  360
                NGHPGVPATHGQV+YTGSYGISSTA TPA+AGHVWMSKQQA   PPP
Rat SOX9  301   NGHPGVPATHGQVSYTGSYGISSTAPTPATAGHVWMSKQQA--PPPPPQQPPQAPQAPQA  358

Hum SOX9  361   QPQAAPPQQPAAPPQQPQAHTLTTLSSEPGQSQRTHIKTEQLSPSHYSEQQQHSPQQIAY  420
                 PQ   P  QP    PQQ QAHTLTTLSSEPGQSQRTHIKTEQLSPSHYSEQQQHSPQQI+Y
Rat SOX9  359   PPQQQAPPQPQQAPQQQQAHTLTTLSSEPGQSQRTHIKTEQLSPSHYSEQQQHSPQQISY  418

Hum SOX9  421   SPFNLPHYSPSYPPITRSQYDYTDHQNSSSYYSHAAGQGTGLYSTFTYMNPAQRPMYTPI  480
                SPFNLPHY+PSYP ITRSQYDYTDHQNS SYYSHAAGQG+GLYSTFTYMNPAQRPMYTPI
Rat SOX9  419   SPFNLPHYNPSYPTITRSQYDYTDHQNSGSYYSHAAGQGSGLYSTFTYMNPAQRPMYTPI  478

Hum SOX9  481   ADTSGVPSIPQTHSPQHWEQPVYTQLTRP  509
                ADTSGVPSIPQTHSPQHWEQPVYTQLTRP
Rat SOX9  479   ADTSGVPSIPQTHSPQHWEQPVYTQLTRP  507
```

Figure 9(B)

SEQUENCE LISTING

```
<160> NUMBER OF SEQ ID NOS: 7

<210> SEQ ID NO 1
<211> LENGTH: 509
<212> TYPE: PRT
<213> ORGANISM: human

<400> SEQUENCE: 1

Met Asn Leu Leu Asp Pro Phe Met Lys Met Thr Asp Glu Gln Glu Lys
1               5                   10                  15

Gly Leu Ser Gly Ala Pro Ser Pro Thr Met Ser Glu Asp Ser Ala Gly
            20                  25                  30

Ser Pro Cys Pro Ser Gly Ser Gly Ser Asp Thr Glu Asn Thr Arg Pro
        35                  40                  45

Gln Glu Asn Thr Phe Pro Lys Gly Glu Pro Asp Leu Lys Lys Glu Ser
    50                  55                  60

Glu Glu Asp Lys Phe Pro Val Cys Ile Arg Glu Ala Val Ser Gln Val
65                  70                  75                  80

Leu Lys Gly Tyr Asp Trp Thr Leu Val Pro Met Pro Val Arg Val Asn
                85                  90                  95

Gly Ser Ser Lys Asn Lys Pro His Val Lys Arg Pro Met Asn Ala Phe
            100                 105                 110

Met Val Trp Ala Gln Ala Ala Arg Arg Lys Leu Ala Asp Gln Tyr Pro
        115                 120                 125

His Leu His Asn Ala Glu Leu Ser Lys Thr Leu Gly Lys Leu Trp Arg
    130                 135                 140

Leu Leu Asn Glu Ser Glu Lys Arg Pro Phe Val Glu Glu Ala Glu Arg
145                 150                 155                 160

Leu Arg Val Gln His Lys Lys Asp His Pro Asp Tyr Lys Tyr Gln Pro
                165                 170                 175

Arg Arg Arg Lys Ser Val Lys Asn Gly Gln Ala Glu Ala Glu Glu Ala
            180                 185                 190

Thr Glu Gln Thr His Ile Ser Pro Asn Ala Ile Phe Lys Ala Leu Gln
        195                 200                 205

Ala Asp Ser Pro His Ser Ser Ser Gly Met Ser Glu Val His Ser Pro
    210                 215                 220

Gly Glu His Ser Gly Gln Ser Gln Gly Pro Pro Thr Pro Pro Thr Thr
225                 230                 235                 240

Pro Lys Thr Asp Val Gln Pro Gly Lys Ala Asp Leu Lys Arg Glu Gly
                245                 250                 255

Arg Pro Leu Pro Glu Gly Gly Arg Gln Pro Pro Ile Asp Phe Arg Asp
            260                 265                 270
```

```
Val Asp Ile Gly Glu Leu Ser Ser Asp Val Ile Ser Asn Ile Glu Thr
        275                 280                 285

Phe Asp Val Asn Glu Phe Asp Gln Tyr Leu Pro Pro Asn Gly His Pro
    290                 295                 300

Gly Val Pro Ala Thr His Gly Gln Val Thr Tyr Thr Gly Ser Tyr Gly
305                 310                 315                 320

Ile Ser Ser Thr Ala Ala Thr Pro Ala Ser Ala Gly His Val Trp Met
                325                 330                 335

Ser Lys Gln Gln Ala Pro Pro Pro Pro Gln Gln Pro Pro Gln Ala
                340             345             350

Pro Pro Ala Pro Gln Ala Pro Gln Pro Gln Ala Ala Pro Pro Gln
            355                 360                 365

Gln Pro Ala Ala Pro Pro Gln Gln Pro Gln Ala His Thr Leu Thr Thr
    370                 375                 380

Leu Ser Ser Glu Pro Gly Gln Ser Gln Arg Thr His Ile Lys Thr Glu
385                 390                 395                 400

Gln Leu Ser Pro Ser His Tyr Ser Glu Gln Gln His Ser Pro Gln
                405             410                 415

Gln Ile Ala Tyr Ser Pro Phe Asn Leu Pro His Tyr Ser Pro Ser Tyr
            420                 425                 430

Pro Pro Ile Thr Arg Ser Gln Tyr Asp Tyr Thr Asp His Gln Asn Ser
            435                 440                 445

Ser Ser Tyr Tyr Ser His Ala Ala Gly Gln Gly Thr Gly Leu Tyr Ser
        450                 455                 460

Thr Phe Thr Tyr Met Asn Pro Ala Gln Arg Pro Met Tyr Thr Pro Ile
465                 470                 475                 480

Ala Asp Thr Ser Gly Val Pro Ser Ile Pro Gln Thr His Ser Pro Gln
                485                 490                 495

His Trp Glu Gln Pro Val Tyr Thr Gln Leu Thr Arg Pro
                500                 505

<210> SEQ ID NO 2
<211> LENGTH: 507
<212> TYPE: PRT
<213> ORGANISM: mouse

<400> SEQUENCE: 2

Met Asn Leu Leu Asp Pro Phe Met Lys Met Thr Asp Glu Gln Glu Lys
1               5                   10                  15

Gly Leu Ser Gly Ala Pro Ser Pro Thr Met Ser Glu Asp Ser Ala Gly
            20                  25                  30

Ser Pro Cys Pro Ser Gly Ser Gly Ser Asp Thr Glu Asn Thr Arg Pro
        35                  40                  45

Gln Glu Asn Thr Phe Pro Lys Gly Glu Pro Asp Leu Lys Arg Glu Ser
    50                  55                  60

Glu Glu Asp Lys Phe Pro Val Cys Ile Arg Glu Ala Val Ser Gln Val
65                  70                  75                  80

Leu Lys Gly Tyr Asp Trp Thr Leu Val Pro Met Pro Val Arg Val Asn
                85                  90                  95

Gly Ser Ser Lys Asn Lys Pro His Val Lys Arg Pro Met Asn Ala Phe
            100                 105                 110

Met Val Trp Ala Gln Ala Ala Arg Arg Lys Leu Ala Asp Gln Tyr Pro
        115                 120                 125

His Leu His Asn Ala Glu Leu Ser Lys Thr Leu Gly Lys Leu Trp Arg
```

```
                     130                 135                 140
Leu Leu Asn Glu Ser Glu Lys Arg Pro Phe Val Glu Ala Glu Arg
145                 150                 155                 160

Leu Arg Val Gln His Lys Lys Asp His Pro Asp Tyr Lys Tyr Gln Pro
                    165                 170                 175

Arg Arg Arg Lys Ser Val Lys Asn Gly Gln Ala Glu Ala Glu Glu Ala
                180                 185                 190

Thr Glu Gln Thr His Ile Ser Pro Asn Ala Ile Phe Lys Ala Leu Gln
                195                 200                 205

Ala Asp Ser Pro His Ser Ser Gly Met Ser Glu Val His Ser Pro
210                 215                 220

Gly Glu His Ser Gly Gln Ser Gln Gly Pro Thr Pro Pro Thr Thr
225                 230                 235                 240

Pro Lys Thr Asp Val Gln Ala Gly Lys Val Asp Leu Lys Arg Glu Gly
                245                 250                 255

Arg Pro Leu Ala Glu Gly Gly Arg Gln Pro Pro Ile Asp Phe Arg Asp
                260                 265                 270

Val Asp Ile Gly Glu Leu Ser Ser Asp Val Ile Ser Asn Ile Glu Thr
                275                 280                 285

Phe Asp Val Asn Glu Phe Asp Gln Tyr Leu Pro Pro Asn Gly His Pro
                290                 295                 300

Gly Val Pro Ala Thr His Gly Gln Val Thr Tyr Thr Gly Ser Tyr Gly
305                 310                 315                 320

Ile Ser Ser Thr Ala Pro Thr Pro Ala Thr Ala Gly His Val Trp Met
                    325                 330                 335

Ser Lys Gln Gln Ala Pro Pro Pro Pro Gln Gln Pro Pro Gln Ala
                340                 345                 350

Pro Gln Ala Pro Gln Ala Pro Pro Gln Gln Ala Pro Pro Gln Gln
                355                 360                 365

Pro Gln Ala Pro Gln Gln Gln Ala His Thr Leu Thr Thr Leu Ser
                370                 375                 380

Ser Glu Pro Gly Gln Ser Gln Arg Thr His Ile Lys Thr Glu Gln Leu
385                 390                 395                 400

Ser Pro Ser His Tyr Ser Glu Gln Gln His Ser Pro Gln Gln Ile
                    405                 410                 415

Ser Tyr Ser Pro Phe Asn Leu Pro His Tyr Ser Pro Ser Tyr Pro Pro
                    420                 425                 430

Ile Thr Arg Ser Gln Tyr Asp Tyr Ala Asp His Gln Asn Ser Gly Ser
                    435                 440                 445

Tyr Tyr Ser His Ala Ala Gly Gln Gly Ser Gly Leu Tyr Ser Thr Phe
                    450                 455                 460

Thr Tyr Met Asn Pro Ala Gln Arg Pro Met Tyr Thr Pro Ile Ala Asp
465                 470                 475                 480

Thr Ser Gly Val Pro Ser Ile Pro Gln Thr His Ser Pro Gln His Trp
                    485                 490                 495

Glu Gln Pro Val Tyr Thr Gln Leu Thr Arg Pro
                500                 505

<210> SEQ ID NO 3
<211> LENGTH: 507
<212> TYPE: PRT
<213> ORGANISM: rat

<400> SEQUENCE: 3
```

-continued

```
Met Asn Leu Leu Asp Pro Phe Met Lys Met Thr Asp Glu Gln Glu Lys
1               5                   10                  15

Gly Leu Ser Gly Ala Pro Ser Pro Thr Met Ser Glu Asp Ser Ala Gly
            20                  25                  30

Ser Pro Cys Pro Ser Gly Ser Gly Ser Asp Thr Glu Asn Thr Arg Pro
            35                  40                  45

Gln Glu Asn Thr Phe Pro Lys Gly Glu Pro Asp Leu Lys Lys Glu Ser
    50                  55                  60

Glu Glu Asp Lys Phe Pro Val Cys Ile Arg Glu Ala Val Ser Gln Val
65                  70                  75                  80

Leu Lys Gly Tyr Asp Trp Thr Leu Val Pro Met Pro Val Arg Val Asn
                85                  90                  95

Gly Ser Ser Lys Asn Lys Pro His Val Lys Arg Pro Met Asn Ala Phe
            100                 105                 110

Met Val Trp Ala Gln Ala Ala Arg Arg Lys Leu Ala Asp Gln Tyr Pro
            115                 120                 125

His Leu His Asn Ala Glu Leu Ser Lys Thr Leu Gly Lys Leu Trp Arg
            130                 135                 140

Leu Leu Asn Glu Ser Glu Lys Arg Pro Phe Val Glu Glu Ala Glu Arg
145                 150                 155                 160

Leu Arg Val Gln His Lys Lys Asp His Pro Asp Tyr Lys Tyr Gln Pro
                165                 170                 175

Arg Arg Arg Lys Ser Val Lys Asn Gly Gln Ala Glu Ala Glu Glu Ala
            180                 185                 190

Thr Glu Gln Thr His Ile Ser Pro Asn Ala Ile Phe Lys Ala Leu Gln
        195                 200                 205

Ala Asp Ser Pro His Ser Ser Ser Gly Met Ser Glu Val His Ser Pro
    210                 215                 220

Gly Glu His Ser Gly Gln Ser Gln Gly Pro Pro Thr Pro Pro Thr Thr
225                 230                 235                 240

Pro Lys Thr Asp Val Gln Ala Gly Lys Val Asp Leu Lys Arg Glu Gly
            245                 250                 255

Arg Pro Leu Ala Glu Gly Gly Arg Gln Pro Pro Ile Asp Phe Arg Asp
        260                 265                 270

Val Asp Ile Gly Glu Leu Ser Ser Asp Val Ile Ser Asn Ile Glu Thr
    275                 280                 285

Phe Asp Val Asn Glu Phe Asp Gln Tyr Leu Pro Pro Asn Gly His Pro
    290                 295                 300

Gly Val Pro Ala Thr His Gly Gln Val Ser Tyr Thr Gly Ser Tyr Gly
305                 310                 315                 320

Ile Ser Ser Thr Ala Pro Thr Pro Ala Thr Ala Gly His Val Trp Met
            325                 330                 335

Ser Lys Gln Gln Ala Pro Pro Pro Pro Gln Gln Pro Pro Gln Pro Ala
            340                 345                 350

Pro Gln Ala Pro Gln Ala Pro Gln Gln Ala Pro Pro Gln Pro Gln Pro
        355                 360                 365

Gln Gln Ala Pro Gln Gln Gln Ala His Thr Leu Thr Thr Leu Ser
    370                 375                 380

Ser Glu Pro Gly Gln Ser Gln Arg Thr His Ile Lys Thr Glu Gln Leu
385                 390                 395                 400

Ser Pro Ser His Tyr Ser Glu Gln Gln His Ser Pro Gln Gln Ile
            405                 410                 415

Ser Tyr Ser Pro Phe Asn Leu Pro His Tyr Asn Pro Ser Tyr Pro Thr
```

```
                    420                 425                 430
Ile Thr Arg Ser Gln Tyr Asp Tyr Thr Asp His Gln Asn Ser Gly Ser
            435                 440                 445

Tyr Tyr Ser His Ala Ala Gly Gln Gly Ser Gly Leu Tyr Ser Thr Phe
        450                 455                 460

Thr Tyr Met Asn Pro Ala Gln Arg Pro Met Tyr Thr Pro Ile Ala Asp
465                 470                 475                 480

Thr Ser Gly Val Pro Ser Ile Pro Gln Thr His Ser Pro Gln His Trp
            485                 490                 495

Glu Gln Pro Val Tyr Thr Gln Leu Thr Arg Pro
            500                 505

<210> SEQ ID NO 4
<211> LENGTH: 25
<212> TYPE: RNA
<213> ORGANISM: artificial
<220> FEATURE:
<223> OTHER INFORMATION: siRNA sequence

<400> SEQUENCE: 4
aaaguugucg cucccacuga aguuu                                           25

<210> SEQ ID NO 5
<211> LENGTH: 601
<212> TYPE: DNA
<213> ORGANISM: human

<400> SEQUENCE: 5
ggcttatctg gctcaagact gttctcaatc tgaaatgcca tccctggctt agcatttcct     60
ctctatccta accccaagt aactccacta accccaaat aactccactg tacctcccca     120
aataactcca ctaaccccca aatagctcca ttataactcc ccaaatagct tccactatct    180
cttgttctgc aaacttatgt tccaacaggg ctgagtcttt tgtctgctgc tcagcatcta    240
gaatgacatt tgcgtagaga tgaacagggc actacacagt agcagttaca ggtgagaact    300
gcttacaggg gctggctctg gcagtaatca cactgtaaat caactaaggg agatggtatt    360 tccatttta acatggggaa actgaggctt catgatgtta gaaagtactt gcccgagact    420
aattacaata ctgaatttga attcaggttt aactgaactt cagtaagcat gacatcgcag    480
gagcggccct ccctctaaag atgcggagcc tgcctctgtt cttcttctca gtgtgctcct    540
tcactgggcg agagtgcaag gccatctggc tgcaggtgac aggagtgttc gtcatgctga    600
c                                                                   601

<210> SEQ ID NO 6
<211> LENGTH: 644
<212> TYPE: DNA
<213> ORGANISM: human

<400> SEQUENCE: 6
gcaggctgag aggagaagct actgagtctt aaaggcatat ggccccagca tcccggggcc    60
tgaaagctgt gacaatattg agggtcaaga gtactaaagc ctggagacta gagctgtcat    120
ttctaggctt acaatggctg ccatgtccta ggggttaaag cctaggtcac tgaatgttca    180
gaccactggg agtccagggc ttttttctcca aggacctcag ctgcagcctc tgactctgcc    240
agtaaggcac ttgggtcgga gcacctgtac ctgagaggtt ttctgctact aatatccatc    300
tatgtagagt agagaactcc agcctgataa ctagtaactg ggatagacac tgcttttcct    360
```

```
tgtcctgggt ttacagcttt acccattaag acagtcaggc acgtctatct ccagcctaga      420
gcacaggaca atgcttttgg gcgggcccta aactaagggc aggactgggc gtgtcctgga      480
cctcctccgc acagtgggag gacgcaccgg atgaccgtcg cctgccacgc gccaggcaca      540
gcatgggaag gcgctcctgt tgccggcggc ccttgccggt ggtggcaagt ctgggtgctg      600
cacttctgtt cctgtgcgcc gcgccgcgcg ccctgcgtcc cggt                       644

<210> SEQ ID NO 7
<211> LENGTH: 601
<212> TYPE: DNA
<213> ORGANISM: human

<400> SEQUENCE: 7
tttgcacctg gtttccaatc tttctggtgg cctccatgga tgctcatctc tagggacaac       60
agtgggctga gttattctca atttagtcac caggtggcag cctagaaggc gaaaacttac      120
tgatgattgg aagactggac taggttctgg tctgagaaac cctgtgagtt tgggtgagat      180
ttggggcaga taggtatctg ggttctgggc tgggctcaaa ggaagcagac attccccgag      240
gatgaggcat cctgagaagg acgtggtttt agtgtgagct gggttcccac ccaaaacagg      300
agttagaacc atcgttgcta tttgaagcta aatgtataaa atgtaatttg tttcatagtc      360
tccattaatt gataatcaat tgctatagat cattgtcata acaggaacca attaggtttg      420
ttgaatacta atatcaagtc cttacagggc acgtatccaa cctgaggcta ctcaaatagc      480
tctgcttctc attgaacaca atgaggttta atattaccgc cattgtacag ggaaatggag      540
tacagatggc aggtaagaca ctagtgttgg tgcagcacct catcccatac actcaaggct      600
a                                                                      601
```

INHIBITION OF SOX9 FUNCTION IN THE TREATMENT OF PROTEOGLYCAN-ASSOCIATED PATHOPHYSIOLOGICAL CONDITIONS

FIELD OF THE INVENTION

The present invention relates to a method of treating conditions associated with the production of proteoglycans (PGs). In particular, the present invention relates to methods of treatment in which PG production is regulated by inhibition of SOX9.

BACKGROUND OF THE INVENTION

Altered proteoglycan metabolism has been implicated in a number of conditions including cardiac fibrosis, kidney disease, Pseudoxanthoma elasticum (PXE) and regenerative failure and poor recovery in the injured or diseased nervous system. PXE is a systemic degenerative disorder of connective tissue characterised by progressive mineralisation and fragmentation of elastic fibres and increased deposition of proteoglycans. These alterations in the extracellular matrix lead to a loss of elasticity in the skin, the eyes, and the cardiovascular system. PXE severity is associated with certain variations of XT-II, and it has been shown that overall xylosyltransferase activity is elevated in patients with certain variations of XT-I.

Cardiac fibrosis is a process that is characterized by a massive remodeling of the myocardial extracellular matrix (ECM) and the subsequent substitution of the functional tissue by inelastic fibrotic tissue. These alterations lead to an impaired organ function and finally to chronic heart failure. Up-regulation of proteoglycan expression is a main characteristic for the progression of this myocardial failure. During the fibrotic remodeling of the ventricular tissue, increased levels of the proteoglycans decorin and biglycan were found, confirming the importance of these matrix components in this process The absence of axonal regeneration after spinal cord injury (SCI) has been attributed in part to the nonpermissive environment of the glial scar (Fawcett and Asher 1999). Although macrophages, microglia oligodendrocytes, invading Schwann cells and meningeal fibroblasts contribute to the glial scar, astrocytes predominate (Fawcett and Asher 1999). Reactive astrocytes in the injured CNS are heterogeneous with respect to their production of scar proteins (Fitch and Silver 1997). Whereas in the majority of cases the extracellular matrix molecules (ECM) produced by astrocytes have been shown to inhibit axonal regeneration (Bahr et al. 1995; Davies et al. 1999; McKeon et al. 1991; Reier and Houle 1988), astrocytes also have been shown to secrete ECM molecules that promote axonal growth (McKeon et al. 1991). Thus, astrocytes may promote or inhibit regeneration after SCI depending upon the balance of growth-inhibiting and growth-promoting ECM molecules that they produce.

Chondroitin sulfate proteoglycans (CSPGs) are probably the most important of the inhibitory molecules produced by reactive astrocytes (Eddleston and Mucke 1993; Fawcett and Asher 1999). In vivo and in vitro studies have shown that regenerating axons cease to extend their axons into areas rich in CSPGs (Davies et al. 1997; Davies et al. 1999; McKeon et al. 1991; Zuo et al. 1998). CSPGs share a common structure comprising a central core protein with a number of chondroitin sulfate side chains (Morgenstern et al. 2002). Chondroitin sulfate side chain synthesis is initiated by the addition of xylose onto a serine moiety of the core protein. This function is carried out by the enzyme xylosyltransferase (XT) that exists in two isoforms encoded by two different genes XT-I and XT-II (Gotting et al. 2000). These side chains are subsequently sulfated by either chondroitin 4-sulfotransferase (C4ST) (Yamauchi et al. 2000) or chondroitin 6-sulfotransferase (Fukuta et al. 1995) although in astrocytes C4ST predominates (Gallo and Bertolotto 1990).

Astrocytes can also produce an array of growth promoting molecules including laminin (Liesi and Silver 1988), N-cadherin (Tomaselli et al. 1988), Neural cell adhesion molecule (NCAM) (Neugebauer et al. 1988) and fibronectin (Matthiessen et al. 1989). Using in vitro models of axon growth, laminin and fibronectin have been shown to be good substrates for neurite extension (Costa et al. 2002; Fok-Seang et al. 1995; Hammarback et al. 1988; McKeon et al. 1991; Rogers et al. 1983; Rogers et al. 1987). In vivo models demonstrate that sensory axon regeneration is dependent on astrocyte-associated fibronectin (Davies et al. 1997; Davies et al. 1999; Tom et al. 2004) and that intrathecal administration of laminin-γ1 promotes regeneration in a rat model of SCI (Wiksten et al. 2004).

It would be desirable to identify pathways and factors that differentially regulate the expression of growth-inhibiting molecules such as proteoglycans and growth-promoting molecules such as laminin and fibronectin in order to develop therapies for diseases and other conditions associated with the up-regulation of growth-inhibiting molecules and/or down-regulation of growth-promoting molecules.

SUMMARY OF THE INVENTION

It has now been shown that down-regulation of SOX9 results in decreased production of growth-inhibiting factors such as proteoglycans and increased production of growth-promoting factors such as laminin and fibronectin. It has also been shown that proteoglycans are associated with a multitude of conditions, including pathological conditions, that may be regulated by inhibiting SOX9.

Thus, in one aspect of the present invention, a method of treating a condition associated with the production of at least one proteoglycan in a mammal is provided. The method comprises the step of inhibiting SOX9 activity in the mammal.

In another aspect of the present invention, a method of promoting neuron growth or regeneration in a mammal is provided comprising the step of inhibiting SOX9 activity in the mammal.

In another aspect, a method of treating in a mammal a condition associated with proteoglycan production in a mammal is provided comprising administering to the mammal a therapeutically effective amount of a compound that inhibits SOX9 expression.

In a further aspect of the present invention, a composition for treating in a mammal a condition associated with the production of at least one proteoglycan is provided. The composition comprises an inhibitor of SOX9.

In another aspect of the present invention, a use of a SOX9 inhibitor for the manufacture of a medicament for treating a condition in a mammal that is associated with the production of at least one proteoglycan.

In a further aspect, a method of screening candidate compounds for inhibition of SOX9 is provided. The method comprises the steps of:
a) incubating a candidate compound with a SOX9-expressing cell line comprising a SOX9 reporter construct, said construct comprising a SOX9 binding region linked to a control region that regulates the expression of a reporter gene;
b) measuring the output of the reporter gene, wherein a reduced output of the reporter gene in comparison to a control output obtained in the absence of incubation with the candidate indicates that the candidate compound is a SOX9 inhibitor.

These and other aspects of the present invention are described in the detailed description by reference to the drawings in which:

BRIEF DESCRIPTION OF THE DRAWINGS

FIG. 9 illustrates SOX9 protein sequences (A, B); and

DETAILED DESCRIPTION OF THE INVENTION

Figure 1:
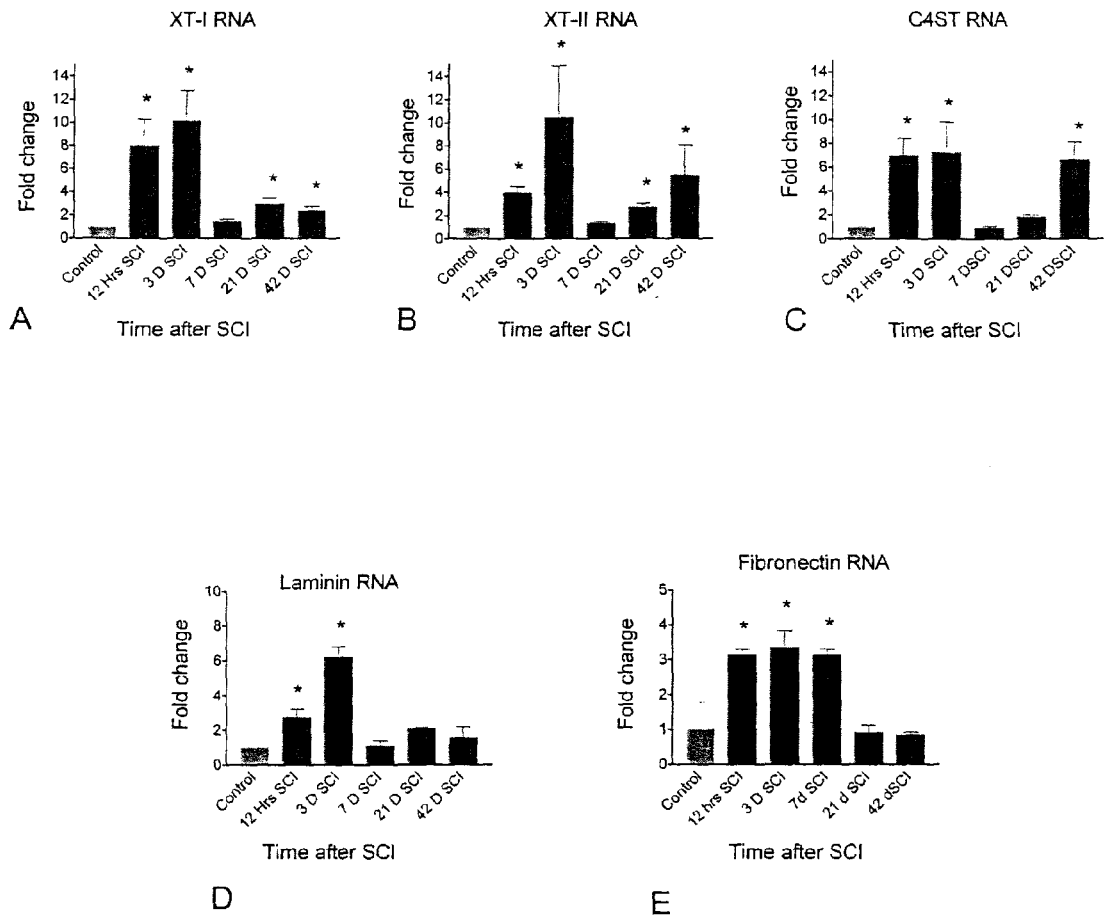
FIG. 1 illustrates by bar graph gene expression profiling of XT-I, XT-II, C4ST, laminin and fibronectin after spinal chord injury (SCI)

A method of treating a condition associated with the production of a proteoglycan in a mammal is provided. The method comprises the step of inhibiting SOX9 activity in the mammal.

SOX9 is a transcription factor required for chondrocyte differentiation and cartilage formation. In humans, SOX9 is a 56 Kda protein having 509 amino acids. SOX9 protein and nucleic acid sequences, including human and other mammalian SOX9 sequences (SEQ ID Nos. 1-3), are exemplified in FIG. 9. For the purposes of the present invention, the term "SOX9" encompasses any functional mammalian SOX9 protein including functional variants thereof. The term "functional" refers to a SOX9 protein that retains the activity of a native, naturally occurring SOX9 protein, for example, regulation of a xylosyltransferase such as XT-1 or a sulfotransferase such as C4ST.

The term "proteoglycan" refers to a family of glycoproteins comprising a core protein and one or more covalently linked glycosaminoglycan chains which are formed, at least in part, by the action of a xylosyltransferase and sulfotransferase. Examples of such proteoglycans include chondroitin sulfate proteoglycans (CSPGs) with core proteins such as phosphan, NG2 and brevican; dermatan sulfate proteoglycans (DSPGs) with core proteins such as decorin; heparin sulfate proteoglycans (HSPGs) with core proteins such as syndecans, glypicans, perlecan, agrin and collagen XVII; and keratin sulfate proteoglycans (KSPGs) with core proteins such as Lumican, Keratocan, Mimecan, Fibromodulin, PRELP, Osteoadherin and Aggrecan. Xylosyltransferases for example, XT-I or XT-II catalyze the first and rate limiting step in the addition of glycosaminoglycan chains to the proteoglycan core protein by the addition of xylose.

The term "production" as it relates to proteoglycans, and conditions associated therewith, refers to the transcriptional regulation of a molecule that modifies or regulates proteoglycan activity wherein the molecule includes, but is not limited to, the core proteoglycan protein, the glycosaminoglycan chains and proteoglycan-synthesizing enzymes such as XT-I, XT-II and C4ST.

The term "mammal" as used herein refers to both human and non-human mammals.

The term "conditions associated with proteoglycan production" is used herein to encompass undesirable conditions and pathologies to which proteoglycan production contributes and in which reduction of at least one proteoglycan ameliorates the condition or pathology. For example, proteoglycan production, such as CSPG is known to contribute to conditions in which normal neuronal growth or neuronal plasticity, including neuronal regeneration, is blocked or otherwise impeded. Examples of such conditions include, but are not limited to, primary conditions of the nervous system that include but are not limited to, spinal cord injury, traumatic brain injury, neurodegenerative diseases, such as Friedreich's ataxia, spinocerebellar ataxia, Alzheimer's disease, Parkinson's Disease, Lou Gehrig's Disease (ALS), demyelinative diseases, such as multiple sclerosis, transverse myelitis, resulting from spinal cord injury, inflammation, and diseases associated with retinal neuronal degeneration such as age-related amblyopia, maculopathies and retinopathies such as viral, toxic, diabetic and ischemic, inherited retinal degeneration such as Kjellin and Barnard-Scholz syndromes, degenerative myopia, acute retinal necrosis and age-related pathologies such as loss of cognitive function. Examples also include conditions that cause cerebrovascular injury including, but not limited to, stroke, vascular malformations, such as arteriovenous malformation (AVM), dural arteriovenous fistula (AVF), spinal hemangioma, cavernous angioma and aneurysm, ischemia resulting from occlusion of spinal blood vessels, including dissecting aortic aneurisms, emboli, arteriosclerosis and developmental disorders, such as spina bifida, meningomyolcoele, or other causes. Proteoglycans are also known to contribute to fibrosis-related pathologies or undesirable conditions and, thus, such pathologies/conditions are encompassed by the term "conditions associated with proteoglycan production". Examples of fibrosis-related pathologies and/or conditions include cystic fibrosis of the pancreas and lungs, heart disease such as cardiomyopathies, cardiac fibrosis including endomyocardial fibrosis and idiopathic myocardiopathy, atherosclerosis, cirrhosis of the liver, idiopathic pulmonary fibrosis of the lung, diffuse parenchymal lung disease, mediastinal fibrosis, myelofibrosis, post-vasectomy pain syndrome, retroperitoneal fibrosis, progressive massive fibrosis, proliferative fibrosis, neoplastic fibrosis, tuberculosis (TB), fibrosis of the spleen from sickle-cell anemia, rheumatoid arthritis, atherosclerosis, nephropathy such as diabetic nephropathy, conditions of the sclera and cornea including corneal scarring and primary disorders of fibrosis such as pseudoxanthoma elasticum (PXE).

In one aspect of the present invention, the method of treating conditions associated with proteoglycan production comprises inhibiting SOX9. As one of skill in the art will appreciate, expression of SOX9 can be inhibited at the nucleic acid level while SOX9 protein activity can be inhibited at the protein level. In either case, the result of inhibiting, or at least reducing, SOX9 activity is achieved. The term "inhibit" as it used herein with respect to SOX9 activity is meant to refer to any reduction of SOX9 activity including both complete as well as partial inhibition of SOX9 activity.

SOX9 activity may be inhibited by inhibiting SOX9 gene expression using well-established methodologies such as anti-sense, snp or siRNA technologies. SOX9-encoding nucleic acid molecules may be used to prepare antisense oligonucleotides effective to bind to SOX9 nucleic and inhibit the expression thereof. The term "antisense oligonucleotide" as used herein means a nucleotide sequence that is complementary to at least a portion of a target SOX9 nucleic acid sequence. The term "oligonucleotide" refers to an oligomer or polymer of nucleotide or nucleoside monomers consisting of naturally occurring bases, sugars, and intersugar (backbone) linkages. The term also includes modified or substituted oligomers comprising non-naturally occurring monomers or portions thereof, which function similarly. Such modified or substituted oligonucleotides may be preferred over naturally occurring forms because of properties such as enhanced cellular uptake, or increased stability in the presence of nucleases. The term also includes chimeric oligonucleotides which contain two or more chemically distinct regions. For example, chimeric oligonucleotides may contain at least one region of modified nucleotides that confer beneficial properties (e.g. increased nuclease resistance, increased uptake into cells) as well as the antisense binding region. In addition, two or more antisense oligonucleotides may be linked to form a chimeric oligonucleotide.

The antisense oligonucleotides of the present invention may be ribonucleic or deoxyribonucleic acids and may contain naturally occurring bases including adenine, guanine, cytosine, thymidine and uracil. The oligonucleotides may also contain modified bases such as xanthine, hypoxanthine, 2-aminoadenine, 6-methyl, 2-propyl and other alkyl adenines, 5-halo uracil, 5-halo cytosine, 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydrodyl guanine and other 8-substituted guanines, other aza and deaza uracils, thymidines, cytosines, adenines, or guanines, 5-trifluoromethyl uracil and 5-trifluoro cytosine.

Other antisense oligonucleotides of the invention may contain modified phosphorous, oxygen heteroatoms in the phosphate backbone, short chain alkyl or cycloalkyl intersugar linkages or short chain heteroatomic or heterocyclic intersugar linkages. For example, the antisense oligonucleotides may contain phosphorothioates, phosphotriesters, methyl phosphonates and phosphorodithioates. In addition, the antisense oligonucleotides may contain a combination of linkages, for example, phosphorothioate bonds may link only the four to six 3'-terminal bases, may link all the nucleotides or may link only 1 pair of bases.

The antisense oligonucleotides of the invention may also comprise nucleotide analogs that may be better suited as therapeutic or experimental reagents. An example of an oligonucleotide analogue is a peptide nucleic acid (PNA) in which the deoxribose (or ribose) phosphate backbone in the DNA (or RNA), is replaced with a polymide backbone which is similar to that found in peptides (P. E. Nielson, et al Science 1991, 254, 1497). PNA analogues have been shown to be resistant to degradation by enzymes and to have extended lives in vivo and in vitro. PNAs also form stronger bonds with a complementary DNA sequence due to the lack of charge repulsion between the PNA strand and the DNA strand. Other oligonucleotide analogues may contain nucleotides having polymer backbones, cyclic backbones, or acyclic backbones. For example, the nucleotides may have morpholino backbone structures (U.S. Pat. No. 5,034,506). Oligonucleotide analogues may also contain groups such as reporter groups, protective groups and groups for improving the pharmacokinetic properties of the oligonucleotide. Antisense oligonucleotides may also incorporate sugar mimetics as will be appreciated by one of skill in the art.

Antisense nucleic acid molecules may be constructed using chemical synthesis and enzymatic ligation reactions using procedures known in the art based on a given SOX9 nucleic acid sequence such as that provided herein. The antisense nucleic acid molecules of the invention, or fragments thereof, may be chemically synthesized using naturally occurring nucleotides or variously modified nucleotides designed to increase the biological stability of the molecules or to increase the physical stability of the duplex formed with mRNA or the native gene, e.g. phosphorothioate derivatives and acridine substituted nucleotides. The antisense sequences may also be produced biologically. In this case, an antisense encoding nucleic acid is incorporated within an expression vector that is then introduced into cells in the form of a recombinant plasmid, phagemid or attenuated virus in which antisense sequences are produced under the control of a high efficiency regulatory region, the activity of which may be determined by the cell type into which the vector is introduced.

In another embodiment, siRNA technology can be applied to inhibit expression of SOX9. Application of nucleic acid fragments such as siRNA fragments that correspond with regions in a SOX9 gene and which selectively target a SOX9 gene may be used to block SOX9 expression. Such blocking occurs when the siRNA fragments bind to the SOX9 gene thereby preventing translation of the gene to yield functional SOX9.

SiRNA, small interfering RNA molecules, corresponding to SOX9 are made using well-established methods of nucleic acid syntheses as outlined above with respect to antisense oligonucleotides. Since the structure of target SOX9 genes is known, fragments of RNA that correspond therewith can readily be made. The effectiveness of selected siRNA to block SOX9 activity can be confirmed using a SOX9-expressing cell line. Briefly, selected siRNA may be incubated with a SOX9-expressing cell line under appropriate growth conditions. Following a sufficient reaction time, i.e. for the siRNA to bind with SOX9 mRNA to result in decreased levels of the SOX9 mRNA, the reaction mixture is tested to determine if such a decrease has occurred. Suitable siRNA will prevent processing of the SOX9 gene to yield functional SOX9 protein. This can be detected by assaying for SOX9 activity in a cell-based assay, for example, to identify expression of a reporter gene that is regulated by SOX9 binding, as described in more detail herein.

It will be appreciated by one of skill in the art that siRNA fragments useful in the present method may be derived from specific regions of SOX9-encoding nucleic acid which may provide more effective inhibition of gene expression, for example, the 5' end of the gene. In addition, as one of skill in the art will appreciate, useful siRNA fragments may not correspond exactly with a SOX9 target gene, but may incorporate sequence modifications, for example, addition, deletion or substitution of one or more of the nucleotide bases therein, provided that the modified siRNA retains it ability to bind to the target SOX9 gene. Selected siRNA fragments may additionally be modified in order to yield fragments that are more desirable for use. For example, siRNA fragments may be modified to attain increased stability in a manner similar to that described for antisense oligonucleotides.

Once prepared, oligonucleotides determined to be useful to inhibit SOX9 gene expression, such as antisense oligonucleotides and siRNA, may be used in a therapeutic method to treat a mammal having a condition associated with neuronal injury or degeneration. A suitable oligonucleotide may be introduced into tissues or cells of the mammal using techniques in the art including vectors (retroviral vectors, adenoviral vectors and DNA virus vectors) or by using physical techniques such as microinjection.

SOX9 activity may also be inhibited at the protein level, for example, using inhibitors designed to block SOX9 either directly or indirectly. SOX9 inhibitors may include biological compounds, and synthetic small molecules or peptide mimetics, for example, based on such biological compounds.

Biological SOX9 inhibitors also include immunological inhibitors such as monoclonal antibodies prepared using the well-established hybridoma technology developed by Kohler and Milstein (Nature 256, 495-497(1975)). Hybridoma cells can be screened immunochemically for production of antibodies specifically reactive with a selected SOX9 region and the monoclonal antibodies can be isolated. The term "antibody" as used herein is intended to include fragments thereof which also specifically react with a SOX9 protein according to the invention, as well as chimeric antibody derivatives, i.e., antibody molecules resulting from the combination of a variable non-human animal peptide region and a constant human peptide region.

Candidate SOX9 inhibitors such as synthetic small molecules or peptide mimetics may also be prepared, for example, based on known biological inhibitors, but which incorporate desirable features such as protease resistance. Generally, such peptide mimetics are designed based on techniques well-established in the art, including computer modelling.

Candidate inhibitors may be screened for inhibitory activity by assaying for SOX9 activity in a cell-based system. Suitable assays utilize primary or established SOX9-expressing cell lines, such astrocyte, cardiac fibroblast, kidney mesangial, or corneal cell lines. SOX9 activity may be monitored in such cell lines by measuring the level of one or more markers of SOX9 inhibition including, but not limited to, mRNA or protein levels of SOX9, a proteoglycan such as CSPG, HSPG or KSPG, a xylotransferase such as XT-I, XT-II, a sulfotransferase such as C4ST, protein levels of laminin or fibronectin and other outputs such as protein activity, protein modifications, cell function, cell activities, and the like. In the presence of a compound which inhibits SOX9, proteoglycan, enzyme and SOX9 levels are each reduced in comparison to control levels determined in a SOX9-expressing cell line which is incubated in the absence of the candidate compound, while levels of laminin and fibronectin increase in comparison to a control. Proteoglycan levels can be readily detected immunologically, using labelled antibodies directed to selected proteoglycans, such as CS56 (Sigma) directed to CSPG, or by staining, for example, using safranin-O. As will be appreciated by one of skill in the art, the levels of markers of SOX9 inhibition can also be determined using one or more of a number of standard techniques such as slot blots or western blots (for protein quantitation) or Q-PCR (for mRNA quantitation) in primary astrocyte cultures or in another suitable cell culture following incubation with the candidate inhibitor for a suitable period of time, for example 24-48 hours.

In another SOX9 screening assay, a SOX9-expressing cell line comprising a SOX9 reporter construct may be used. The construct incorporates a SOX9 binding region linked to control region, e.g. a promoter, that regulates the expression of a reporter gene. The Sox9 binding region may be, for example, repeats of the SOX9 binding site, or a SOX9 binding region from the promoter region of the XT-1 gene or from the C4ST gene as exemplified herein in the specific examples that follow. The reporter gene may be any gene whose output, e.g. expression, protein levels, protein activity, protein modifications, cell function, cell activities, and the like, is readily detectable, for example, the luciferase gene, the green fluorescent protein gene and the β-galactosidase gene. In the presence of SOX9, the control region is turned on and the reporter gene is expressed. In the presence of a SOX9 inhibitor, the control region is not turned on, and expression of the reporter gene is reduced or prevented.

In another embodiment, a method of screening for Sox9 inhibitors may comprise a combination of determinations as set out above, for example, a determination of the level of one or more markers of SOX9 inhibition as described above, as well as measuring the output of a reporter construct. The measure of markers of SOX9 inhibition may be accomplished using techniques established in the art including, for example, immunological techniques, staining, and quantitative PCR. This combination method serves to confirm that any noted inhibition of SOX9 is regulating proteoglycan production.

A therapeutic inhibitor of SOX9 may be administered to a mammal in need of treatment of a condition associated with proteoglycan production as previously described. Inhibitors of SOX9 expression and inhibitors of SOX9 activity, including both nucleic acid based inhibitors and other inhibitors, may be administered in combination with a suitable pharmaceutically acceptable carrier. The expression "pharmaceutically acceptable" means acceptable for use in the pharmaceutical and veterinary arts, i.e. not being unacceptably toxic or otherwise unsuitable. Examples of pharmaceutically acceptable carriers include diluents, excipients and the like. Reference may be made to "Remington's: The Science and Practice of Pharmacy", 21st Ed., Lippincott Williams & Wilkins, 2005, for guidance on drug formulations generally. The selection of adjuvant depends on the type of inhibitor and the intended mode of administration of the composition. In one embodiment of the invention, the compounds are formulated for administration by infusion, or by injection either subcutaneously, intravenously, intrathecally, intraspinally or as part of an artificial matrix, and are accordingly utilized as aqueous solutions in sterile and pyrogen-free form and optionally buffered or made isotonic. Thus, the compounds may be administered in distilled water or, more desirably, in saline, phosphate-buffered saline or 5% dextrose solution. Compositions for oral administration via tablet, capsule or suspension are prepared using adjuvants including sugars, such as lactose, glucose and sucrose; starches such as corn starch and potato starch; cellulose and derivatives thereof, including sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil and corn oil; polyols such as propylene glycol, glycerine, sorbital, mannitol and polyethylene glycol; agar; alginic acids; water; isotonic saline and phosphate buffer solutions. Wetting agents, lubricants such as sodium lauryl sulfate, stabilizers, tableting agents, anti-oxidants, preservatives, colouring agents and flavouring agents may also be present. Aerosol formulations, for example, for nasal delivery, may also be prepared in which suitable propellant adjuvants are used. Other adjuvants may also be added to the composition regardless of how it is to be administered, for example, anti-microbial agents may be added to the composition to prevent microbial growth over prolonged storage periods.

The inhibitor may be administered in combination with other therapeutic agents to enhance the treatment protocol.

The present invention advantageously provides a means of inhibiting the activity of proteoglycans, such as CSPGs, KSPGs and HSPGs, when the activity thereof is associated with undesirable conditions, for example, the formation of scar tissue (e.g. glial scar formation in connection with neurons), and excess connective tissue (e.g. in fibrosis-related conditions) which inhibit normal growth, regeneration or activity of cells or connective tissue within an affected region. In accordance with the present invention, inhibition of SOX9 advantageously down-regulates the activity or production of proteoglycans associated with such conditions by down-regulating enzymes involved in the synthesis thereof, e.g. XT-1, XT-11 and C4ST. In addition, the inhibition of SOX9 results in an increased production of growth-promoting molecules such as fibronectin and laminin. Thus, the present invention provides a means by which a mammal afflicted with an undesirable condition associated with proteoglycan production can be treated to inhibit factors generally involved in growth-inhibition as well as promote growth.

Embodiments of the invention are described in the following specific examples which are not to be construed as limiting.

Example 1

SOX9 Effect on Axonal Growth Regulators

Materials and Methods
Animals and Surgeries

All protocols for these experiments were approved by the University of Western Ontario Animal Care Committee in accordance with the policies established in the Guide to Care and Use of Experimental Animals prepared by the Canadian Council on Animal Care. Thirty-two female Wistar Rats (Charles River) weighing 250-300 g were premedicated with diazepam (3.5 mg/kg, i.p.) and atropine (0.05 mg/kg s.c.). Anesthesia was induced with 4% halothane and maintained with 1-1.5% halothane. A laminectomy was performed to expose the T4 spinal segment and a modified aneurysm clip calibrated to a 50 g weight, was passed extradurally around the cord. Severe spinal cord compression was achieved by releasing the clip and allowing it to remain closed for one minute (Fehlings and Tator 1995). The surgical wounds were closed and the rats were given 5 mg/kg of Baytril (Bayer Inc.), 5 mL of 0.9% saline twice daily for three days and buprenophine (0.01 mg/kg s.c.) as needed. Bladders were manually emptied twice daily. After 12 hours or 3, 7, 21 or 42 days, the rats were anesthetized with 1:2 ratio of ketamine:xylazine (0.13 ml/100 g) the injured segment of the spinal cord was removed, immediately homogenized in ice cold Trizol solution (Invitrogen) and the RNA extracted as described (Carmel et al. 2001).

Primary Cell Culture

Primary astrocyte cultures were prepared from newborn rats at postnatal day 1 (P1) (Wilson and Dixon 1989). The upper portion of the skull was removed and the meninges carefully dissected away to avoid contamination of the culture with fibroblasts. The neocortices were removed, placed into serum-free advanced D-MEM (Dulbecco's Modified Eagle Medium, Invitrogen), homogenized by pipeting and gravity-filtered through 70 µm cell strainer (Falcon). The cells were plated onto 6-well dishes (Falcon). The percentage of GFAP-expressing cells in these cultures was found to be >95%. Cytokine treatments of primary astrocytes with PDGF, IL-6, TNFα and TGFβ2 (R and D systems) and bFGF2 (Invitrogen) were carried out for 12 hours. RNA was extracted using the Qiagen (Germany) RNA-easy kit following manufacturer's specifications. The transfections of primary astrocytes with SiRNAs and the CMV-SOX9 expression construct were conducted using Lipofectamine 2000 (Invitrogen) according to manufacturer's specifications in 6-well dishes (Falcon). The siRNA (AAAGUUGUCGCUC-CCACUGAAGUUU) (SEQ ID No. 4) was used at a concentration of 150 pM. The universal negative control scrambled SiRNA was used according to manufacturer's (Invitrogen) specifications. Transfection efficiencies with a fluorescently-tagged control SiRNA was 35%-40%. The CMV-SOX9 construct has previously been described (Foster et al. 1994; Lefebvre et al. 1997) and plasmid transfection efficiency estimated by cotransfection with a CMV-GFP construct was approximately 10%.

RNA In Situ Hybridization

Rats were perfused with 4% paraformaldehyde 21 or 42 days after SCI, their spinal cords removed and cryostat-sectioned horizontally at 16 µm. RNA in situ hybridization for XT-I expression was carried out using standard procedures (Schaeren-Wiemers and Gerfin-Moser 1993). A 491 bp fragment from nucleotides 226-717 (NCBI accession number XM 341912.1, incorporated herein by reference) of the rattus XT-I gene was amplified by reverse transcription PCR, and subcloned into pGEM-T Easy (Promega). An antisense riboprobe was generated using the T7 RNA polymerase and digoxigenin-labeled UTP. The riboprobe signal was detected using an anti-digoxigenin alkaline phosphatase-conjugated antibody (1:500; Roche) and 4-nitro blue tetrazolium chloride with 5-bromo-4-chloro-3-indolyl-phosphate (NBT-BCIP; Roche). Sense riboprobes were used as negative controls.

Immunohistochemistry

Rats were perfused with 4% paraformaldehyde 21 or 42 days after SCI, their spinal cords removed and cryostat-sectioned horizontally at 16 µm. Slides were processed for immunohistochemistry using anti-GFAP antibodies (BD Pharmigen) at a 1:200 dilution to identify reactive astrocytes, anti-CD11b antibodies (Sigma) at a 1:200 dilution to identify macrophages or with an antibody, CS56 (Sigma), that recognizes the terminal portions of chondroitin sulfate-4 or -6 side chains and thus detects a variety of CSPGs (Avnur and Geiger 1984; Fawcett and Asher 1999) at a 1:50 dilution.

Slot Blot Analysis

Tissue and cell samples were lysed in RIPA buffer [20 mM, Tris-HCl (pH 7.6), 150 mM NaCl, 0.5% sodium deoxycholate, 1% Triton X-100, 0.1% SDS]. Then the proteins (3 µg/well) were transferred to polyvinylidene difluoride membranes (Millipore, Mississauga, ON) using Bio-Dot slot blot apparatus (BioRad, Mississauga, ON). The membranes were first blocked in 10% non-fat powdered milk and then incubated with primary antibody at 1:200 dilution overnight for CS-56 (Sigma, Missouri, USA). Following the incubation with HRP-conjugated donkey anti-mouse antibody (1:10,000), membranes were incubated in ECL plus Western blotting detection reagents (Amersham, Buckinghamshire, UK) according to the manufacturer's specifications. Immunoreactive bands were scanned by an imaging densitometer (BioRad GF-700 Imaging Densitometer, Mississauga, ON);

and results were quantified using Multi-Analist software (BioRad, Mississauga, ON). All values were normalized by dividing the densitometric values for expression by the values for expression of β-actin (anti-β-actin antibody from Sigma 1:10,000 dilution).

In Silico Analysis of Putative Promoter Regions

The putative promoter regions of CBGs were identified using ELDORADO software. Transcription start sites were automatically assigned to the genes using databases integrated in to the promoter identification program ELDORADO (Cohen et al. 2006). Promoter nucleotide sequences were analyzed using DIALIGN software tool (Genomatix Software, GmbH).

Microarray Hybridization and Data Analysis

All GeneChips were processed at the London Regional Genomics Centre (Robarts Research Institute, London, Ontario, Canada). RNA quality was assessed using the Agilent 2100 Bioanalyzer (Agilent Technologies Inc., Palo Alto, Calif.) and the RNA 6000 Nano kit (Caliper Life Sciences, Mountain View, Calif.). RNA was extracted from a 2 mm portion of spinal cord centered on T4 (at the epicenter of the lesion in the spinal cord injured rats). Biotinylated complimentary RNA (cRNA) was prepared from 10 μg of total RNA as per the Affymetrix GeneChip Technical Analysis Manual (Affymetrix, Santa Clara, Calif.). Double-stranded cDNA was synthesized using SuperScriptII (Invitrogen, Carlsbad, Calif.) and oligo $(dT)_{24}$ primers. Biotin-labeled cRNA was prepared by in vitro transcription using the BioArray High-Yield RNA Transcript Labeling kit (Enzo Biochem, New York) incorporating biotinylated UTP and CTP. 10 μg of labeled cRNA was hybridized to RAE230A GeneChips for 16 hours at 45° C. GeneChips were scanned with the Affymetrix GeneChip Scanner 3000 (Affymetrix, Santa Clara, Calif.). Probe signal intensities were generated with GCOS1.3 (Affymetrix Inc., Santa Clara, Calif.) using default values for the Statistical Expression algorithm parameters and a Target Signal of 150 for all probe sets and a Normalization Value of 1. Gene expression level data was generated using the RMA preprocessor in GeneSpring GX 7.0 (Agilent Technologies Inc., Palo Alto, Calif.). Data were then transformed, (measurements less than 0.01 set to 0.01) and normalized per chip to the $50^{th}$ percentile, and per gene to median.

Quantitative Polymerase Chain Reaction (Q-PCR).

First strand cDNA was synthesized from 1 μg RNA per condition (cell culture or animal tissue) using the High Capacity cDNA Archive Kit according to the manufacturer protocol (Applied Biosystems Foster City Calif.). The primer probe sets, optical adhesive covers, and PCR plates were purchased from Applied Biosystems (Foster City, Calif.). The probes were labeled with 5' FAM and with 3'TAMRA as quencher with the exception of the ribosomal probe, which was labeled with 5' VIC. For Taq Man assays the thermal cycler conditions were 10 minutes at 95° C. followed by 40 cycles of 30 seconds at 95° C. followed by 30 seconds at 60° C. A standard curve of cycle thresholds using cDNA serial dilutions was established and used to calculate abundance of each target mRNA. Technical triplicates and at least biological triplicates were run on all conditions tested. Values were normalized to the amounts of 18S mRNA as determined by Q-PCR. The data were analyzed by a two way ANOVA following by a Bonferroni test with Dunn's correction for multiple comparisons or Dunnet's procedure when comparisons were made with a single variable (control). Student's t-test was used when only two groups were compared.

Primer-Probe Sets for TaqMan Gene Expression Assays:

| Target Gene | Probe and Primer catalog number (from Applied Biosystems) |
|---|---|
| 18S | 4308329 |
| XT-I | 1391062A |
| XT-II | Mm00517563_m1 |
| C4ST | Mm00517563_m1 |
| Laminin-γ1 | Mm00711808_m1 |
| SOX9 | Mm 0048840_m1 |
| TGβ2 | Rn00579674_m1 |
| IL-6 | Rn00561420_m1 |
| Fibronectin-I | Rn00569575_m1 |
| GFAP | Rn00566603_m1 |

Results

Expression Profiles of XT-I, XT-II and C4ST after SCI

XT-I, XT-II and C4ST all showed similar patterns of gene expression after SCI as detected by Q-PCR (FIG. 1 A-C). The mRNA levels of these genes peak from 12 hours to 3 days following SCI, then return to baseline levels by 7 days post-injury. XT-I, XT-II and C4ST increase their expression levels at later time points so that by 42 days post-injury the increase in mRNA levels of XT-I, XT-II and C4ST is 2, 5 and 7-fold respectively relative to controls. For ease of writing XT-I, XT-II and C4ST will hereon in be referred to as CBGs with the understanding that they represent only a subset of the enzymes necessary for the generation of chondroitin sulfate side chains. Increases in the expression of XT-I, XT-II and C4ST after SCI are accompanied by increased CSPG levels as measured by slot blot analysis using protein extracts from the spinal lesion and an antibody, CS-56. The expression profiles as revealed by Q-PCR demonstrates that like CBGs, laminin and fibronectin mRNA levels are elevated early after SCI but unlike CBGs, they are not elevated at later time points (21 and 42 days) post-injury (FIG. 1 D, E).

Identification of the Cellular Source of CBG mRNA by In Situ Hybridization

To determine the cellular source of CBG mRNA after SCI, RNA in situ hybridization analysis on sections of rat injured spinal cords were conducted with a XT-I anti-sense riboprobe. Immunohistochemistry on these same sections using an anti-CD11b mAb to detect macrophages and an anti-GFAP antibody to detect astrocytes indicated that 6 weeks after injury both these cell types express XT-I in the lesion.

IL-6, PDGF, and TGFβ2 are Putative Regulators of XT-I, XT-II and C4ST

Figure 2:
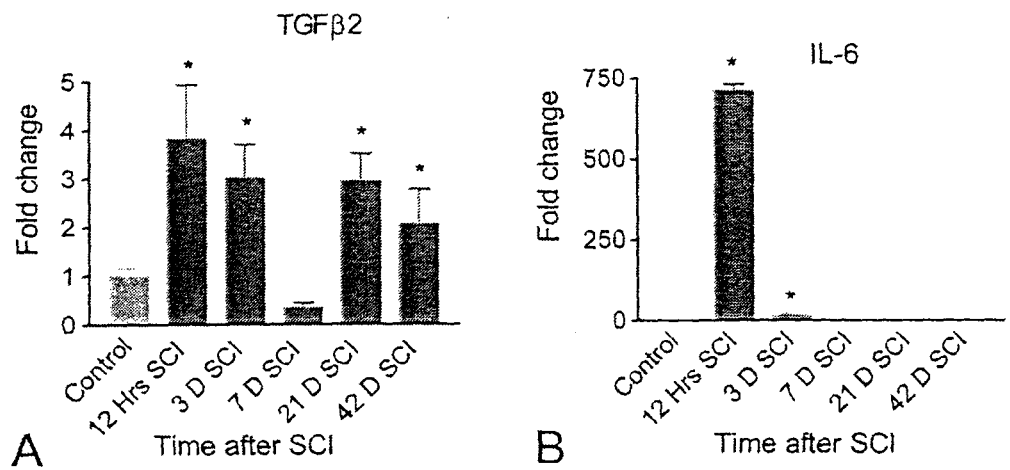
FIG. 2 illustrates by bar graph the Quantitative PCR (Q-PCR) confirmation of the expression profiles of (A) TGFβ2 and (B) IL-6 in the spinal lesion.

The first strategy used to identify potential positive regulators of XT-I, XT-II and C4ST gene transcription was based on the premise that a subset of molecules that are able to up-regulate expression will show expression patterns similar to the Q-PCR-delineated expression patterns of XT-I, XT-II and C4ST as described above. For example, an inducer of XT-I, XT-II and C4ST expression will itself show elevated levels of expression when XT-I, XT-II and C4ST expression levels are high and low levels of expression when XT-I, XT-II and C4ST expression levels are low. Thus, gene expression profiles were analyzed in the rat injured spinal cord using an Affymetrix platform (the Affymetrix Rat 230A gene chip) after a clip compression SCI in the rat. Since inflammation is known to be a key regulator of fibrosis and scarring, that analysis was restricted to known cytokine mediators of inflammation. From this group 3 cytokines, IL-6, TGFβ2 and PDGF with expression profiles most similar to the expression profiles of XT-I, XT-II and C4ST were identified. The microarray-delineated expression profile for two of these cytokines, TGF2 and IL-6, was verified by Q-PCR on mRNA isolated from lesion sites at 12 hours, 3, 7, 21 and 42 days after SCI (FIG. 2 A, B). In agreement with the microarray data, these cytokines demonstrated rapid increases in mRNA levels 12 hours after SCI followed by a decrease to baseline levels by 7 days after SCI and a subsequent increase in TGFβ2 but not IL-6 mRNA at 21 and 42 days after SCI. Thus these cytokines and XT-I, XT-II and C4ST have similar patterns of expression after SCI.

In Silico Analysis of Promoter Regions of XT-I, XT-II and C4ST

The second strategy used to identify regulators of XT-I, XT-II and C4ST was to identify transcription factor binding sites in common to the promoters of all three genes. This strategy was based on the premise that, if XT-I, XT-II and C4ST constitute part of a gene battery, then they would be controlled by an overlapping set of transcription factors. The putative promoter regions of XT-I, XT-II and C4ST were defined using Genomatix suite software (Genomatix Software GmbH). To reduce the possibility of incorrectly identifying putative transcription factor binding sites, the promoter sequences of human, rat and mouse XT-I, XT-II and C4ST genes were compared and only the transcription factors with predicted binding sites in all three genes in all three species were accepted as candidate regulators of XT-I, XT-II and C4ST. Using Genomatix software, SOX9 was identified as a transcription factor that regulates XT-I, XT-II and C4ST expression.

The Genomatix-predicted SOX9 binding site in the XT-1 gene's promoter is highlighted in the following nucleotide sequence upstream of the XT-1 genes transcriptional start site:

From the upstream region of XT-I gene a sequence including:

(SEQ ID No. 5)
```
  1 GGCTTATCTG GCTCAAGACT GTTCTCAATC TGAAATGCCA TCCCTGGCTT AGCATTTCCT

61 CTCTATCCTA ACCCCCAAGT AACTCCACTA ACCCCCAAAT AACTCCACTG TACCTCCCCA

121 AATAACTCCA CTAACCCCCA AATAGCTCCA TTATAACTCC CCAAATAGCT TCCACTATCT

181 CTTGTTCTGC AAACTTATGT TCCAACAGGG CTGAGTCTTT TGTCTGCTGC TCAGCATCTA

241 GAATGACATT TGCGTAGAGA TGAACAGGGC ACTACACAGT AGCAGTTACA GGTGAGAACT

301 GCTTACAGGG GCTGGCTCTG GCAGTAATCA CACTGTAAAT CAACTAAGGG AGATGGTATT

361 TCCATTTTAA ACATGGGGAA ACTGAGGCTT CATGATGTTA GAAAGTACTT GCCCGAGACT

421 AATTACAATA CTGAATTTGA ATTCAGGTTT AACTGAACTT CAGTAAGCAT GACATCGCAG

481 GAGCGGCCCT CCCTCTAAAG ATGCGGAGCC TGCCTCTGTT CTTCTTCTCA GTGTGCTCCT

541 TCACTGGGCG AGAGTGCAAG GCCATCTGGC TGCAGGTGAC AGGAGTGTTC GTCATGCTGA

601 C
```

The bioinformatics analyses predicted SOX9 binding sequences in two separate regions upstream of the C4ST gene's transcriptional start site. Sequences from these two areas are shown below. The Genomatix-predicted SOX9 binding sites are highlighted.

Area 1:

(SEQ ID No. 6)
```
  1 GCAGGCTGAG AGGAGAAGCT ACTGAGTCTT AAAGGCATAT GGCCCCAGCA TCCCGGGGCC
 61 TGAAAGCTGT GACAATATTG AGGGTCAAGA GTACTAAAGC CTGGAGACTA GAGCTGTCAT
121 TTCTA█████████████████ATGTCCTA GGGGTTAAAG CCTAGGTCAC TGAATGTTCA
181 GACCACTGGG AGTCCAGGGC TTTTTCTCCA AGGACCTCAG CTGCAGCCTC TGACTCTGCC
241 AGTAAGGCAC TTGGGTCGGA GCACCTGTAC CTGAGAGGTT TTCTGCTACT AATATCCATC
301 TATGTAGAGT AGAGAACTCC AGCCTGATAA CTAGTAACTG GGATAGACAC TGCTTTTCCT
361 TGTCCTGGGT TTACAGCTTT ACCCATTAAG ACAGTCAGGC ACGTCTATCT CCAGCCTAGA
421 GCACAGGACA ATGCTTTTGG GCGGGCCCGA AACGAAGGGC AGGACTGGGC GTGTCCTGGA
481 CCTCCTCCGC ACAGTGGGAG GACGCACCGG ATGACCCTCG CCTGCCACGC GCCAGGCACA
541 GCATGGGAAG GCGCTCCTGT TGCCGGCGGC CCTTGCCGGT GGTGGCAACT CTGGGTGCTG
601 CACTTCTGTT CCTGTGCGCC GCGCCGCGCG CCCTGCGTCC CGGT
```

Area 2:

(SEQ ID NO. 7)
```
  1 TTTGCACCTG GTTTCCAATC TTTCTGGTGG CCTCCATGGA TGCTCATCTC TAGGGACAAC
 61 AGTGGGCTGA GTTATTCTCA ATTTAGTCAC CAGGTGGCAG CCTAGAAGGC GAAAACTTAC
121 TGATGATTGG AAGACTGGAC TAGGTTCTGG TCTGAGAAAC CCTGTCACTT TGGGTGAGAT
181 TTGGGGCAGA TAGGTATCTG GGTTCTGGGC TGGGCTCAAA GGAAGCAGAC ATTCCCCGAG
241 GATGAGGCAT CCTGAGAAGG ACGTGGTTTT AGTGTGAGCT GGGTTCCCAC CCAAAACAGG
301 AGTTAGAACC ATCGTTGCTA TTTGAAGCTA AATGTATAAA ATGTAATTTG TTTCATAGTC
361 ████████████████████████ TGCTATACAT CATTGTCATA ACAGGAACCA ATTAGGTTTG
421 TTGAATACTA ATATCAAGTC CTTACAGGGC ACGTATCCAA CCTGAGGCTA CTCAAATAGC
481 TCTGCTTCTC ATTGAACACA ATGAGGTTTA ATATTACCGC CATTGTACAG GGAAATGGAG
541 TACAGATGGC AGGTAAGACA CTAGTGTTGG TGCAGCACCT CATCCCATAC ACTCAAGGCT
601 A
```

Figure 3:
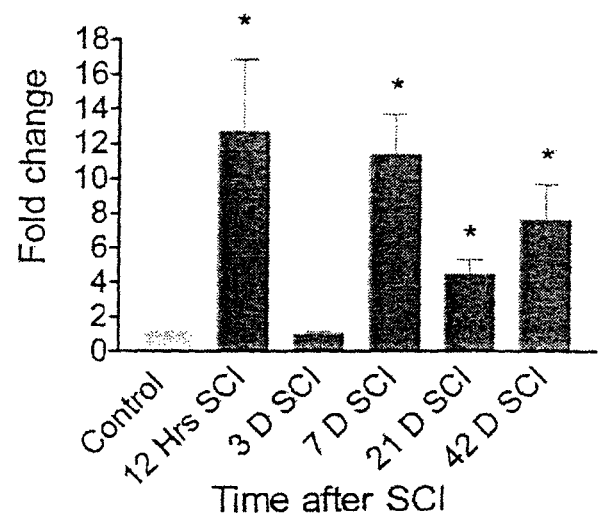
FIG. 3 is a bar graph illustrating SOX9 mRNA levels in the spinal cord following injury as determined using Q-PCR.

To investigate the likelihood that SOX9 may regulate CBG expression, SOX9 expression was analyzed after SCI in the rat by Q-PCR. SOX9 showed a rapid 12-fold increase in expression levels at 12 hours post-injury. By the third day after SCI the mRNA levels of SOX9 were not different from the control but they increased again 11-fold relative to control one week after SCI and remained elevated through to 42 days post-injury (FIG. 3). Immunohistochemistry using an antibody that recognizes the phosphorylated active form of SOX9 and an anti-GFAP antibody clearly shows co-expression of SOX9 and GFAP in the spinal cord lesion at 42 days post-injury.

Characterization of CBG Expression in Primary Astrocyte Cultures

Figure 4:
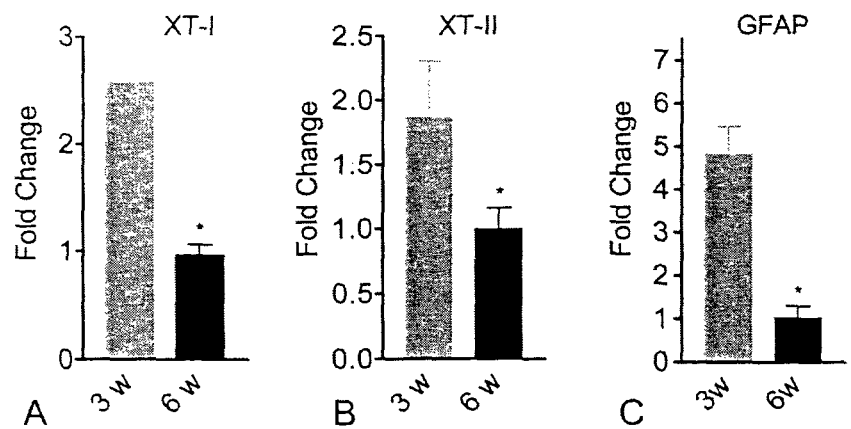
FIG. 4 illustrates the expression levels of XT-I (A), XT-II (B) and GFAP (C) in primary astrocyte cultures.
Figure 5:
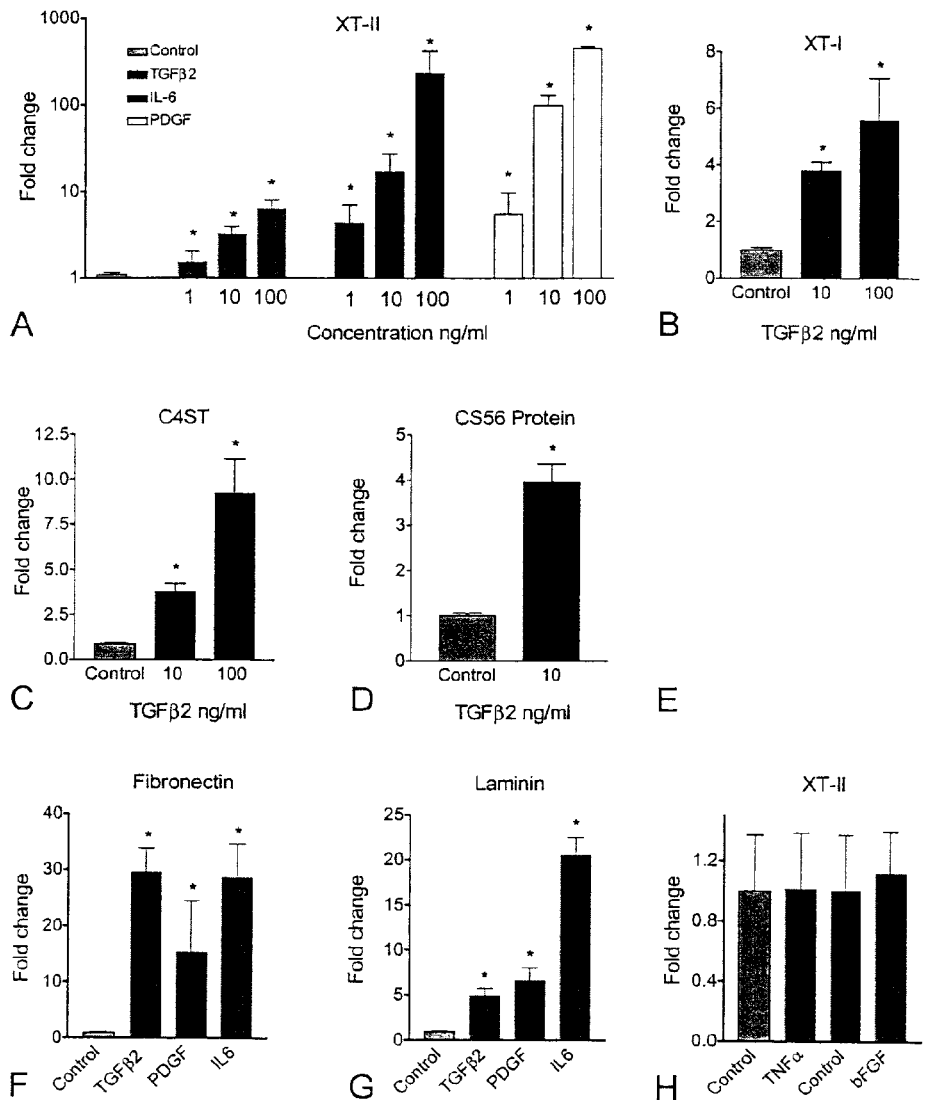
FIG. 5 illustrates the effect of TGFβ2, IL-6 and PDGF on XT-I (B), XT-II (A), C4ST (C), CS56 protein (D), fibronectin (E) and laminin (F) gene expression in primary astrocytes in comparison to the effect of TNFα or bFGF (H)

To test putative regulators of XT-I, XT-II and C4ST, a cell culture system was developed to reflect the cellular make-up of the injured spinal cord. Since astrocytes are a major source of CSPGs at the glial scar (Alonso and Privat 1993; Fawcett and Asher 1999; Reier and Houle 1988) and express CBGs and SOX9, primary astrocyte cultures were used to investigate the transcriptional regulation of XT-I, XT-II and C4ST. To provide baseline values on the expression of these genes in primary β after 3 and 6 weeks in culture. The levels of XT-I and XT-II mRNA in primary astrocytes was approximately 2-fold greater in 3-week than in 6-week cultures (FIG. 4 A, B). The higher levels of XT-I and -II mRNA in 3 week-old primary astrocyte cultures reflected that these cultures were in an activated state induced by the isolation procedure. This was supported by the observation that the expression of GFAP, a gene expressed by reactive astrocytes following CNS injury (Janeczko 1988; Vijayan et al. 1990) was also elevated in 3 week-old compared to 6 week-old astrocyte cultures (FIG. 4 C).

TGF2, IL-6 and PDGF Increase the Expression Levels of XT-I, XT-II and C4ST

Figure 6:
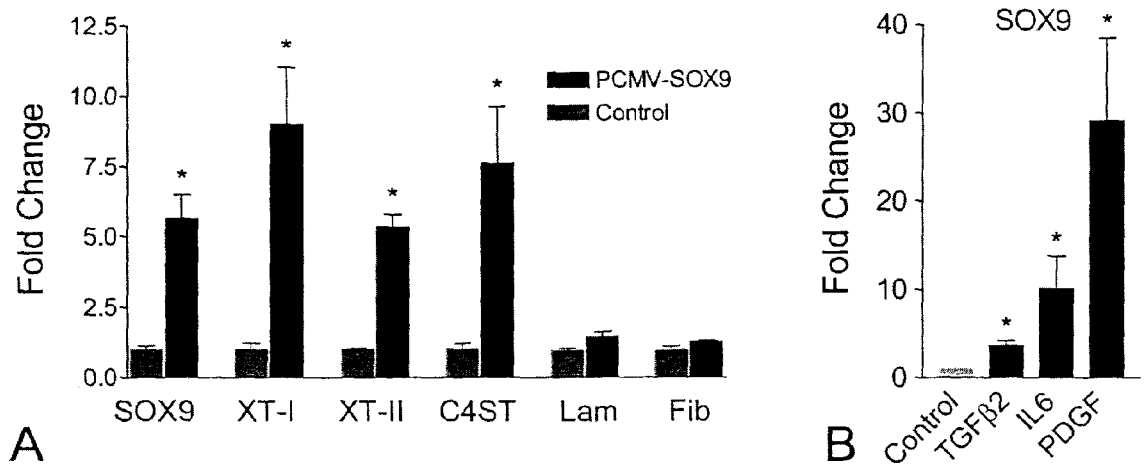
FIG. 6 illustrates the Q-PCR indication that SOX9 expression up-regulates XT-I, XT-II and C4ST but not laminin or fibronectin gene expression (A) and that TGFβ2, IL-6 and PDGF increase the expression of SOX9.

To evaluate TGFβ2, PDGF and IL-6 as candidate XT-I, XT-II and C4ST transcriptional regulators, rat primary astrocyte cultures were exposed to 1, 10 or 100 ng/ml of each cytokine. After a 12 hour cytokine exposure, XT-I, XT-II and C4ST mRNA levels were measured relative to untreated cultures by Q-PCR. Six week-old cultures were used as, by this time point, the astrocytes are quiescent (as evidenced by reduced GFAP expression) and baseline levels of XT-I, XT-II and C4ST genes are low. Treatment of 6 week-old primary astrocyte cultures with TGF☐2, IL-6 and PDGF resulted in a strong, concentration-dependent up-regulation of XT-II mRNA above control values (FIG. 6 A). Similar increases in expression were observed for XT-I and C4ST (FIG. 6 B, C). The increased expression of CBGs in these cultures was matched by an increased expression of CSPG protein as assessed by slot blot analysis (FIG. 6 D). Fibronectin and laminin expression were similarly increased following these cytokine treatments (FIG. 6 F, G). In support of this experimental approach, cytokines such as TNFβ2 and bFGF that have expression profiles different from the expression profiles of XT-I, XT-II and C4ST were found to have no effect on XT-II mRNA levels in primary astrocytes (FIG. 6 H).

SOX9 Regulates CBG but not Laminin mRNA Levels

To test whether SOX9 regulates expression of XT-I, XT-II and C4ST in vitro, primary astrocytes were transfected with a SOX9 expression construct and assessed for CBG mRNA levels by Q-PCR 48 hours later. CMV-driven SOX9 expression resulted in significant increases in XT-I, XT-II and C4ST mRNA (FIG. 6 A). The levels of fibronectin and laminin mRNA in these same cultures were unaffected by SOX9 over-expression. To determine whether IL-6, PDGF and TGF☐2 might increase XT-I, XT-II and C4ST gene expression by up-regulating SOX9 expression, the expression levels of SOX9 mRNA were assayed after these cytokine treatments in primary astrocyte cultures. The cytokine treatments (TGFβ2, IL-6 and PDGF) that up-regulated the expression of XT-I, XT-II and C4ST caused a significant increase in SOX9 mRNA levels (FIG. 6 B).

Figure 7:
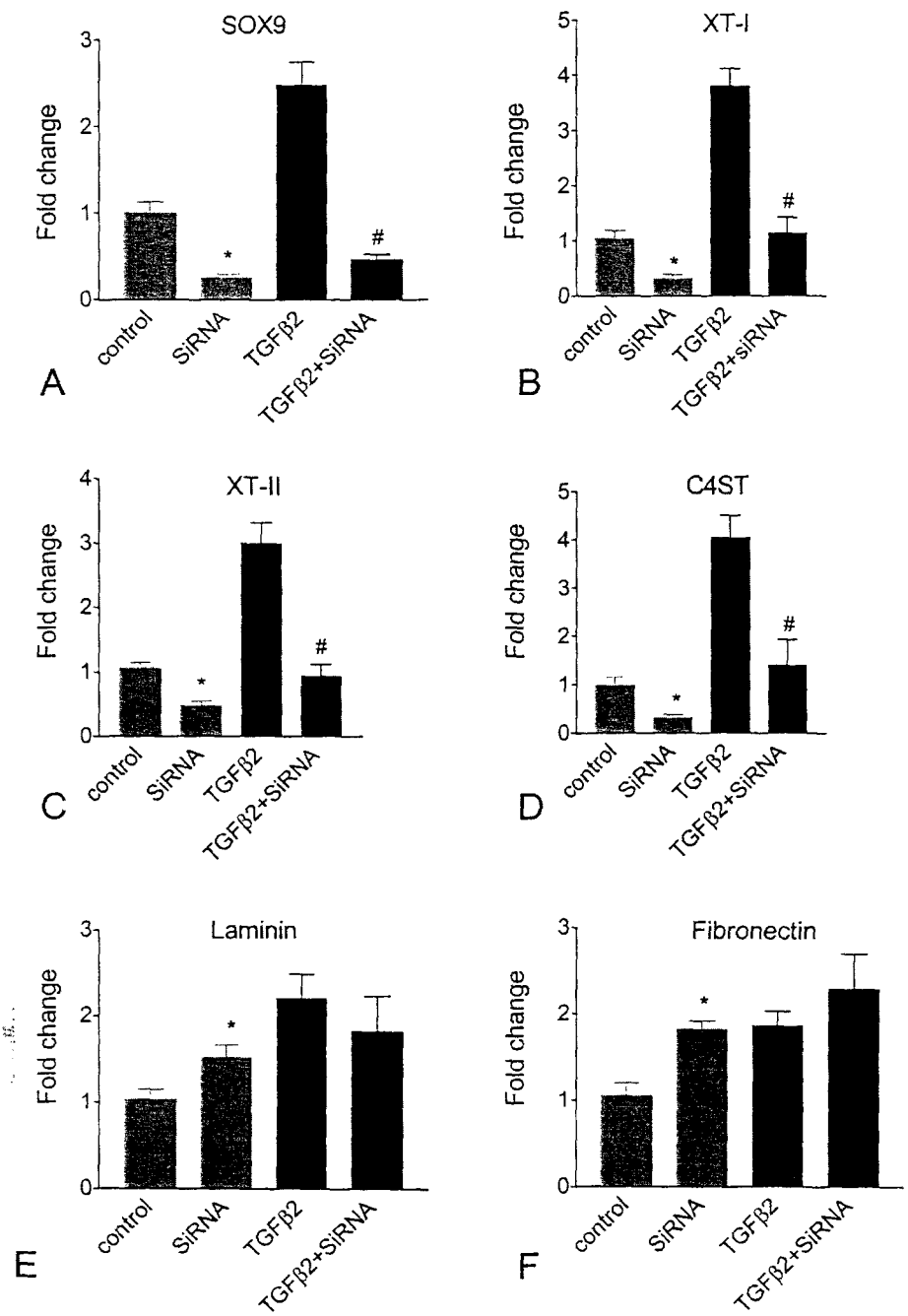
FIG. 7 illustrates Q-PCR results indicating that SOX9 expression is necessary for basal and TGFβ2-driven expression of XT-I (B), XT-II (C) and C4ST (D), and that laminin and fibronectin gene expression is increased in the absence of SOX9.

To test the effect of SOX9 knock-down on the expression of XT-I, XT-II and C4ST, a control (scrambled) small interfering RNA (SiRNA) or an anti-SOX9 SiRNA was transfected into primary astrocytes and mRNA levels of SOX9, XT-I, XT-II and C4ST were assayed by Q-PCR 12 hours later. Transfection of primary astrocytes with an anti-SOX9 siRNA resulted in a 75±12% reduction in SOX9 mRNA levels and a 71±5.5% reduction in XT-I mRNA (FIG. 7 A, B). Transfection of TGF☐☐ treated primary astrocytes with the anti-SOX9 SiRNA resulted in a 87±13% reduction in SOX9 mRNA levels and a 68±6.4% reduction in XT-I mRNA, while TGF☐☐ treatment alone resulted in increased SOX9 and XT-1 mRNA levels. Similar reductions were observed also in XT-II and C4ST expression in the presence of anti-SOX9 SiRNA in both TGFβ2⁻-treated and untreated cultures (FIG. 7 C, D). SOX9 knock-down did not decrease laminin or fibronectin gene expression. (FIG. 7 E, F).

The results clearly show that SOX9 expression is both necessary and sufficient for CBG expression in primary astrocytes and that cytokine up-regulation of CBG expression is SOX9 dependent. The anti-SOX9 SiRNA transfections show that laminin and fibronectin expression are negatively regulated by SOX9.

Example 2

Effect of Anti-CD11d mAb-Treatment on SCI

Experimental Methods
Animals and Surgeries
  As described in Example 1.
Microarray Analysis All GeneChips were processed at the London Regional Genomics Centre (Robarts Research Institute, London, ON). The quality of each RNA sample was assessed using the Agilent 2100 Bioanalyzer (Agilent Technologies Inc., Calif., USA) and the RNA 6000 Nano kit (Caliper Life Sciences, California, USA). Biotinylated complementary RNA (cRNA) was prepared from 10 μg of total RNA as per the Affymetrix GeneChip Technical Analysis Manual (Affymetrix, California, USA). Double-stranded cDNA was synthesized using SuperScriptII (Invitrogen, California, USA) and oligo $(dT)_{24}$ primers. Biotin-labeled cRNA was prepared by cDNA in vitro transcription using the BioArray High-Yield RNA Transcript Labeling kit (Enzo Biochem, New York, USA) incorporating biotinylated UTP and CTP. The biotin-labeled cRNA (10 μg) was hybridized to RAE230A GeneChips for 16 h at 45° C. as described in the Affymetrix Technical Analysis Manual (Affymetrix, California, USA). RNA samples from each animal (3 anti-CD11d-treated and 3 untreated animals at each time point) were hybridized to separate GeneChips. Three RNA samples from 3 different uninjured animals were likewise hybridized to 3 separate GeneChips to provide control levels of gene expression. The GeneChips were stained with Streptavidin-Phycoerythrin, followed by an antibody solution, and a second Streptavidin-Phycoerythrin solution; a GeneChip Fluidics Station 400 performed all liquid handling. GeneChips were scanned with the Affymetrix GeneChip Scanner 3000 (Affymetrix, California, USA). Probe signal intensities were generated using GCOS1.3 (Affymetrix Inc., California, USA) with default values for the statistical expression algorithm parameters and a target signal of 150 for all probe sets and a normalization value of 1. Gene level data were generated using the RMA preprocessor in GeneSpring GX 7.3 (Agilent Technologies Inc., California, USA). The data were transformed (measurements less than 0.01 were set to 0.01) and normalized per chip to the $50^{th}$ percentile, and per gene to median. Statistically significant changes in mRNA levels that correlated to treatment and/or time post-injury was compiled using a two-way ANOVA (p<0.05). The Benjamini and Hochberg false discovery test that corrects for multiple testing was used to determine differences between mean values. All data analysis and mining were performed using GeneSpring GX 7.3 (Agilent Technologies Inc., California, USA).

Quantitative Polymerase Chain Reaction (Q-PCR)

In this study, 1 □g RNA per condition (cell culture or animal tissue) was used to synthesize first strand cDNA, using High Capacity cDNA Archive Kit according to the manufacturer's specification (Applied Biosystems, California, USA). The primer probe sets, optical adhesive covers, and PCR plates were purchased from Applied Biosystems California, USA. These probes were labeled at the 5' end with FAM (Applied Biosystems) and at the 3' end with TAMRA (Applied Biosystems) as quencher with the exception of the ribosomal probe, which was labeled with 5' VIC (Applied Biosystems). For the Taq Man assays the thermal cycler conditions were 10 minutes at 95° C., followed by 40 cycles of 30 seconds at 95° C. to denature the DNA and 30 seconds at 60° C. to anneal and extend the template. A standard curve of cycle thresholds using cDNA serial dilutions was established and used to calculate abundance of a target gene. The values were normalized to the amounts of 18S mRNA. The data were analyzed using one way ANOVA followed by a Bonferroni test for multiple comparisons.

TaqMan Gene Expression Primer-Probe Sets:

| Target Gene | Probe and Primer Catalog Number (Applied Biosystems) |
|---|---|
| CD8β | Rn00580581_m1 |
| CD4 | Rn00562286_m1 |
| XT-I | 1391062A |
| XT-II | Mm00517563_m1 |
| C4ST | Mm00517563_m1 |
| Laminin | Mm00711808_m1 |
| SOX-9 | Mm 0048840_m1 |
| TGβ-2 | Rn00579674_m1 |
| IL-6 | Rn00561420_m1 |
| Fibronectin | Rn00569575_m1 |
| BMP-7 | Rn 0158889_m1 |

Tissue Processing

At 3, 7 or 21 days post-SCI, control and anti-CD11d treated rats (N=5 for each group at each time point) were given an intraperitoneal overdose of 26% Ketamine (100 mg/ml, Vetalar, Bioniche, Belleville, ON) and 0.06% Xylazine (20 mg/ml, Rompun, Bayer, Toronto, ON) in a 2:1 mixture. Each rat was intracardially perfused with 250 ml of oxygenated tissue culture medium (pH 7.4, Dulbecco's modified Eagle medium, Gibco Invitrogen Corp, Burlington, ON) followed by 500 ml of 4% formaldehyde fixative in 0.1 M phosphate buffer solution (PBS, pH 7.4), both at room temperature. A section of spinal cord centered around the lesion was removed such that it was 0.5 cm rostral and caudal to the lesion site (T3-T4). All cords were processed as previously described (Saville et al., 2004). Eight sets of slides containing serial 16 □m thick sections from each animal were collected and used in the immunohistochemical analyses.

Results

Wound Healing and Scar Genes

Figure 8:
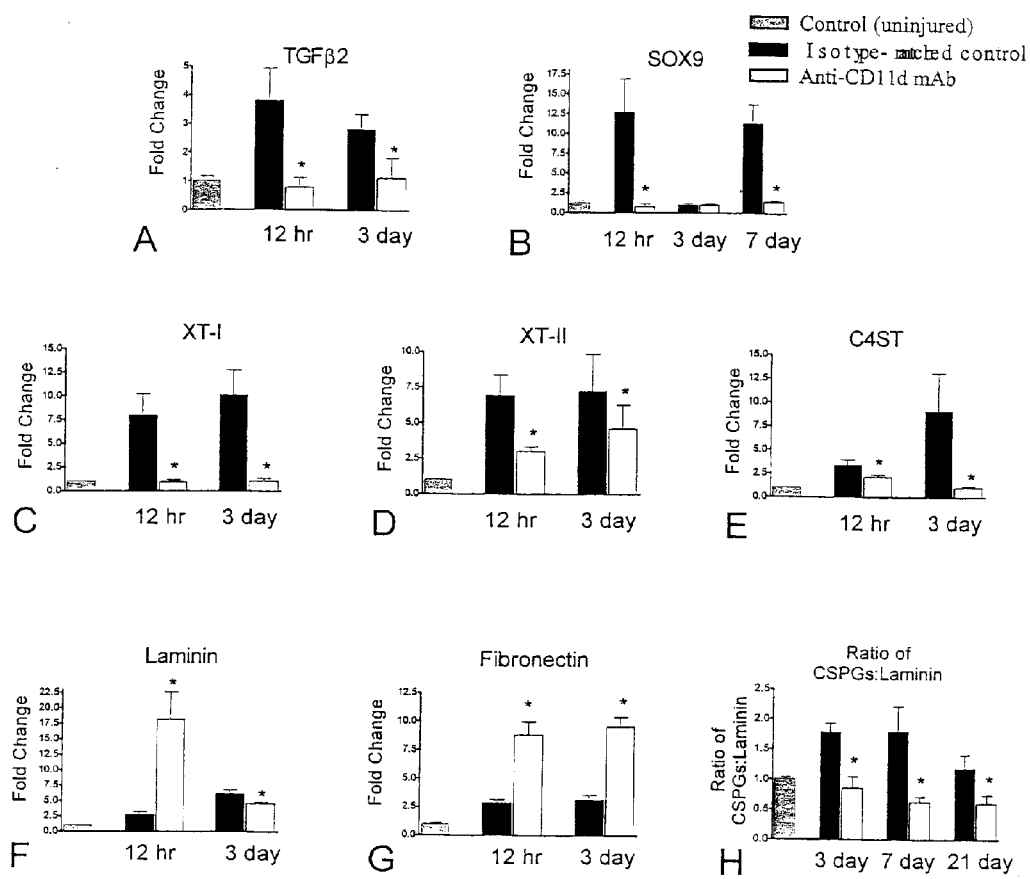
FIG. 8 graphically shows the Q-PCR results indicating that anti-CD11d mAb treatment reduces TGFβ2 (A), SOX9 (B), XT-I (C), XT-II (D) and C4ST (E) expression while increasing laminin (F) and fibronectin (G) gene expression at acute time points after SCI.

Altered expression of immune response genes could have profound effects on the expression of genes associated with wound healing. CSPGs, laminin and fibronectin are key components of the glial scar that may determine the degree of neurological recovery possible in spinal cord-injured animals (Bradbury et al., 2002; Grimpe and Silver, 2004). Thus, the possibility that improved recovery in the anti-CD11d mAb-treated rats is due in part to changes in the expression of these genes involved in scar formation was investigated. Q-PCR confirmed that IL-6 and TGF□2 mRNA are down-regulated acutely in treated rats (FIG. 8 A). Reduced cytokine expression is matched by acute reductions in SOX9, XT-I, XT-II and C4ST mRNA levels in anti-CD11d mAb-treated rats (FIG. 8 C-E). In keeping with the finding that SOX9 inhibits the expression of laminin and fibronectin in primary astrocyte cultures, the decrease in SOX9 expression in anti-CD11d mAb treated rats was accompanied by increases in laminin and fibronectin mRNA levels (FIG. 8 F, 8G). Slot blot analyses using an anti-laminin antibody and the CS56 antibody that recognizes a variety of CSPGs (Avnur and Geiger, 1984) indicates that these differences in mRNA levels correlate with significant decrease in the ratio of CSPG:laminin protein in the lesions of anti-CD11d mAb-treated rats (FIG. 8 H). Immunohistochemistry on sections from the lesion epicenters demonstrates the changed nature of the glial scar. Using alternating tissue sections taken from the same SCI rat lesion areas used in the CD8α analysis, double labeling with anti-laminin and CS56 antibodies, anti-neurofilament and anti-CS56 antibodies and anti-laminin and anti-neurofilament antibodies shows increased amounts of laminin relative to CSPGs in the anti-CD11d-treated spinal cord-injured rats and an increase in neurofilament stained axons in the lesion epicenters that is most prominent in laminin-rich areas. Thus, increased axon sprouting or sparing is associated with increased laminin and decreased CSPG production in rats treated with the anti-CD11d mAb.

Example 3

Expression of CSPGs in Various Neuropathological Samples

To elucidate the role of CSPGs in human SCI, traumatic brain injury (TBI), hemorrhagic stroke, ischemic stroke, and Alzheimers Disease (AD), immunohistochemistry was carried out on sections from subjects with these conditions. Histological sections were obtained from the Pathology department at London's University Hospital (Dr. David Ramsay). Sections were stained with CS56 (an antibody recognizing many CSPGs) in combination with antibodies raised against either GFAP (to stain for reactive astrocytes), SMI32 (neurons), or CD68 (microglia/macrophages).

Methods

Tissue Processing

Human sections for all neuropathological conditions were obtained from Dr. David Ramsay (Department of Pathology, University of Western Ontario). Mice were cardiac perfused with 4% paraformaldehyde to fix tissue. Brains were dissected out and embedded in paraffin. 10 μm sections were cut using a microtome, and mounted on slides.

Immunohistochemistry

All sections were processed for deparaffinization using a series of xylene and ethanol washes, followed by incubation in 10% hydrogen peroxide in methanol. After deparaffinization, antigen retrieval was carried out by boiling sections in citric acid (pH 6.0) for 15 minutes. Sections were then washed for 10 minutes in PBS, and blocked in 10% Goat Serum and 0.5% Triton-X in PBS for 1 hour.

Human sections were double stained with a combination of primary antibodies against CS56 (1/100, Sigma, St. Louis, Mo.), SOX9 (1/100, Chemicon, Temecula, Calif.), GFAP (1/100, Molecular Probes, Carlsbad, Calif.), SMI32 (1/100, Covance, Princeton, N.J.), and CD68 (1/100, Dako, Carpintera, Calif.). Mouse MCAO sections were double stained with a combination of primary antibodies against SOX9, GFAP, and TUJ1 (1/100 Chemicon, Temecula, Calif.). Secondary antibodies for different combinations were used as shown in Tables 2 and 3.

TABLE 2

Secondary antibody combinations and concentrations for different combinations of primary antibodies in human fluorescent double staining experiments.

| Primary Antibody Combination | Secondary 1 | Secondary 2 |
| --- | --- | --- |
| CS56/GFAP | Fluorescein IgM | Rhodamine IgG1 |
| CS56/SMI32 | Fluorescein IgM | Rhodamine IgG2b |
| CS56/CD68 | Fluorescein IgM) | Rhodamine IgG1 |
| CS56/SOX9 | Fluorescein IgM | Alexafluor 594 Goat Anti-rabbit IgG |
| SOX9/GFAP | Alexafluor 594 Goat Anti-rabbit IgG | Alexafluor 488 Goat Anti-mouse IgG |
| SOX9/SMI32 | Alexafluor 594 Goat Anti-rabbit IgG | Alexafluor 488 Goat Anti-mouse IgG |
| SOX9/CD68 | Alexafluor 594 Goat Anti-rabbit IgG | Alexafluor 488 Goat Anti-mouse IgG |

TABLE 3

Secondary antibody combinations and concentrations for different combinations of primary antibodies in mouse MCAO fluorescent double staining experiments.

| Primary Antibody Combination | Secondary 1 | Secondary 2 |
| --- | --- | --- |
| SOX9/GFAP | Alexafluor 594 Goat Anti-rabbit IgG | Alexafluor 488 Goat Anti-mouse IgG |
| SOX9/Tuj1 | Alexafluor 594 Goat Anti-rabbit IgG | Alexafluor 488 Goat Anti-mouse IgG |

All Alexafluor-conjugated secondary antibodies were obtained from Molecular Probes (Carlsbad, Calif.). All other secondary antibodies were obtained from Jackson ImmunoResearch. Sox9-positive cells were counted manually in 3 different sections from each patient.

Real-Time Quantitative PCR

Mice were anesthetised with ketamine:xylazine (2:1) and perfused with saline. Brains were dissected out and the cortices removed. The cortices were then placed in Trizol and homogenized with a tissue homogenizer. RNA was extracted using, and stored at −80° C. CDNA was then synthesized. Primer probe sets for SOX9 and 18S (identified previously) were used to quantify gene expression using quantitative PCR.

Results

The immunohistochemistry demonstrated CSPG expression in all 5 neuropathological conditions studied. In control sections immunohistochemistry demonstrated that CSPGs are not expressed outside of perineuronal nets (PNNs) in uninjured healthy brains. Double labelling with anti-GFAP and CS56 antibodies showed that reactive astrocytes are present in the region of CS56 immunoreactivity. In human TBI, hemorrhagic stroke, and ischemic stroke, the reactive astrocytes can be seen around the outer edge of the areas rich in CSPGs. In SCI and AD, the reactive astrocytes are present throughout the CSPG-rich region. Neurons associated with CSPG-rich areas were only observed in sections from ischemic stroke. CD68-positive microglia and macrophages were also observed in areas immunoreactive for CSPGs.

SOX9 Expression in Human Neuropathological Sections

Since previous studies in our laboratory have shown that the transcription factor SOX9 is necessary and sufficient for the expression of enzymes involved in chondroitin sulphate side chain synthesis, the expression of SOX9 was examined in CSPG-rich regions. SOX9 positive nuclei were observed in all areas of CS56-immunoreactivity. To elucidate cellular localization of SOX9, double staining was carried out with an anti-SOX9 antibody, in combination with one of anti-GFAP, anti-SMI32, or anti-CD68 antibodies, to detect reactive astrocytes, neurons, and macrophages, respectively. SOX9 was found in the nuclei of reactive astrocytes in all neuropathological conditions studied, but not in the uninjured brain. In addition, SOX9 was found in the nuclei and cytoplasm of neurons in healthy and injured or diseased brains and in the nuclei of CD68 positive cells. The expression in healthy uninjured neurons probably reflects the involvement of SOX9 in the expression of CSPGs that constitute part of the PNNs.

Concurrent with the human studies, a mouse model of stroke (MCAO) was studied to confirm the expression and cellular localization of SOX9 in cerebrovasular injury. SOX9 was found in the nuclei of reactive astrocytes in MCAO-injured brains, but not in uninjured brains. SOX9 was also found in the nuclei of neurons in both healthy and injured brains. Through quantitative PCR, it was shown that SOX9 mRNA expression is elevated in the injured cortex of MCAO mice as compared to the uninjured control.

Example 4

Assay to Screen for SOX9 Inhibitors

Proteoglycans, and in particular CSPGs, produced by reactive astrocytes in the injured or diseased central nervous system (CNS) are inhibitory to regeneration. Using both gain-of-function and loss-of-function experiments, the transcription factor SOX9 has been found to be both necessary and sufficient to up-regulate the expression of XT-I, XT-II and C4ST in primary astrocyte cultures. It has also been demonstrated that, whereas SOX9 up-regulates the production of CSPGs, it down-regulates the expression of laminin and fibronectin.

An assay has been developed to screen for SOX9 inhibitors.

Astrocytes, such as wither primary astrocytes (rodent or human) or an established astrocyte cell line designated as Neu7 (Fok-Seang, Smith-Thomas et al. 1995), were transfected with a SOX9 reporter construct under standard conditions. The SOX9 reporter construct (a gift from Dr. Michael Underhill, University of British Columbia) has 4 repeats of the SOX9 binding site coupled to the mouse Col2a1 minimal promoter (−89 to +6) cloned upstream of a luciferase gene in the plasmid pGL4 (Promega) (Weston, Chandraratna et al. 2002). Changes in luciferase levels in transfected cultures is used as a read-out of SOX9 activity. The anti-SOX9 siRNA previously used (or astrocytes from the SOX9 conditional knock out) is used as a positive control and the scrambled siRNA is used as a negative control for this screen. The screen is used to identify compounds that reduce the levels of luciferase activity relative to control wells. Such compounds will be SOX9 inhibiting and will be considered as positive "hits". In a secondary screen false positives that cause a reduction in luciferase activity due to effects on cell viability, will be eliminated by assaying cell death in treated cultures by propidium iodide uptake. When using primary astrocyte cultures the transfection will be normalized to control plasmid co-transfected with the SOX9 reporter construct.

Figure 10:
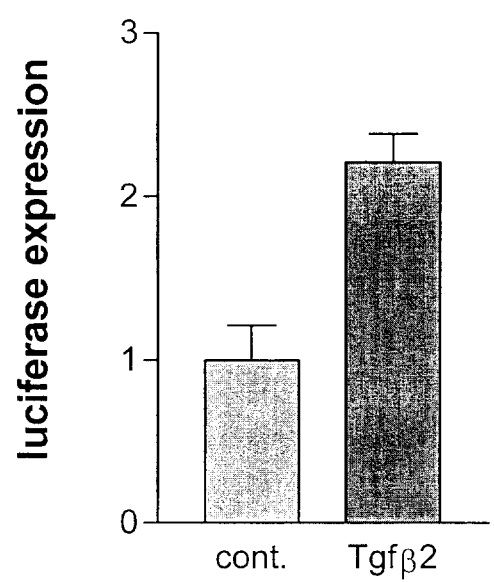
FIG. 10 graphically illustrates increased luciferase activity in a SOX9 luciferase reporter construct following treatment with TGF-β2.

Validation of this screen has been obtained from experiments that have shown that primary astrocytes transfected with the SOX9 luciferase reporter construct demonstrate approximately a 2-fold increase in luciferase activity after treatment with TGF-β2 as TGFβ-2 increases SOX9 expression and activity in primary astrocytes (FIG. 10). Specifically, primary astrocytes obtained from newborn rats were cultured in 6-well dishes for 6 weeks in Advanced-DMEM with 10% FBS. The culture medium was replaced with 2 ml of serum-free Advanced-DMEM with 10 ul of Lipofectamine 2000 (Invitrogen) and 10 ug SOX9-reporter plasmid DNA per well. Transfection efficiency was calculated by co-transfection with a control plasmid. After 24 hours the cells were treated with TGF-β2 (final concentration 10 nM). Twenty-four hours after the TGF-β2 application the cells were lysed and luciferase activity was measured using the Luciferase Assay System (PROMEGA) (according to the manufacturer's protocol) and a luminometer.

FULL CITATIONS FOR REFERENCES REFERRED TO IN THE SPECIFICATION

1. Alonso G, Privat A. 1993. Reactive astrocytes involved in the formation of lesional scars differ in the mediobasal hypothalamus and in other forebrain regions. J Neurosci Res 34(5):523-38.
2. Asher R A, Morgenstern D A, Fidler P S, Adcock K H, Oohira A, Braistead J E, Levine J M, Margolis R U, Rogers J H, Fawcett J W. 2000. Neurocan is upregulated in injured brain and in cytokine-treated astrocytes. J Neurosci 20(7): 2427-38.
3. Avnur Z, Geiger B. 1984. Immunocytochemical localization of native chondroitin-sulfate in tissues and cultured cells using specific monoclonal antibody. Cell 38(3):811-22.
4. Bahr M, Przyrembel C, Bastmeyer M. 1995. Astrocytes from adult rat optic nerves are nonpermissive for regenerating retinal ganglion cell axons. Exp Neurol 131(2):211-20.
5. Blatti S P, Foster D N, Ranganathan G, Moses H L, Getz M J. 1988. Induction of fibronectin gene transcription and mRNA is a primary response to growth-factor stimulation of AKR-2B cells. Proc Natl Acad Sci USA 85(4):1119-23.
6. Bradbury E J, Moon L D, Popat R J, King V R, Bennett G S, Patel P N, Fawcett J W, McMahon S B. 2002. Chondroitinase ABC promotes functional recovery after spinal cord injury. Nature 416(6881):636-40.
7. Carmel J B, Galante A, Soteropoulos P, Tolias P, Recce M, Young W, Hart R P. 2001. Gene expression profiling of acute spinal cord injury reveals spreading inflammatory signals and neuron loss. Physiol Genomics 7(2):201-13.
8. Christner P J, Jimenez S A. 2004. Animal models of systemic sclerosis: insights into systemic sclerosis pathogenesis and potential therapeutic approaches. Curr Opin Rheumatol 16(6):746-52.
9. Cohen C D, Klingenhoff A, Boucherot A, Nitsche A, Henger A, Brunner B, Schmid H, Merkle M, Saleem M A, Koller K P and others. 2006. Comparative promoter analysis allows de novo identification of specialized cell junction-associated proteins. Proc Natl Acad Sci USA 103(15): 5682-7.
10. Costa S, Planchenault T, Charriere-Bertrand C, Mouchel Y, Fages C, Juliano S, Lefrancois T, Barlovatz-Meimon G, Tardy M. 2002. Astroglial permissivity for neuritic outgrowth in neuron-astrocyte cocultures depends on regulation of laminin bioavailability. Glia 37(2):105-13.
11. Davies J E, Tang X, Denning J W, Archibald S J, Davies S J. 2004. Decorin suppresses neurocan, brevican, phosphacan and NG2 expression and promotes axon growth across adult rat spinal cord injuries. Eur J Neurosci 19(5): 1226-42.
12. Davies S J, Fitch M T, Memberg S P, Hall A K, Raisman G, Silver J. 1997. Regeneration of adult axons in white matter tracts of the central nervous system. Nature 390 (6661):680-3.
13. Davies S J, Goucher D R, Doller C, Silver J. 1999. Robust regeneration of adult sensory axons in degenerating white matter of the adult rat spinal cord. J Neurosci 19(14):5810-22.
14. Eddleston M, Mucke L. 1993. Molecular profile of reactive astrocytes—implications for their role in neurologic disease. Neuroscience 54(1):15-36.
15. Eddy A A. 1996. Molecular insights into renal interstitial fibrosis. J Am Soc Nephrol 7(12):2495-508.
16. Fawcett J W, Asher R A. 1999. The glial scar and central nervous system repair. Brain Res Bull 49(6):377-91.
17. Fehlings M G, Tator C H. 1995. The relationships among the severity of spinal cord injury, residual neurological function, axon counts, and counts of retrogradely labeled neurons after experimental spinal cord injury. Exp Neurol 132(2):220-8.
18. Fitch M T, Silver J. 1997. Activated macrophages and the blood-brain barrier: inflammation after CNS injury leads to increases in putative inhibitory molecules. Exp Neurol 148 (2):587-603.
19. Fok-Seang J, Smith-Thomas L C, Meiners S, Muir E, Du J S, Housden E, Johnson A R, Faissner A, Geller H M, Keynes R J and others. 1995. An analysis of astrocytic cell lines with different abilities to promote axon growth. Brain Res 689(2):207-23.
20. Foster J W, Dominguez-Steglich M A, Guioli S, Kowk G, Weller P A, Stevanovic M, Weissenbach J, Mansour S, Young I D, Goodfellow P N and others. 1994. Campomelic dysplasia and autosomal sex reversal caused by mutations in an SRY-related gene. Nature 372(6506):525-30.
21. Fukuta M, Uchimura K, Nakashima K, Kato M, Kimata K, Shinomura T, Habuchi O. 1995. Molecular cloning and expression of chick chondrocyte chondroitin 6-sulfotransferase. J Biol Chem 270(31):18575-80.
22. Furumatsu T, Tsuda M, Taniguchi N, Tajima Y, Asahara H. 2005. Smad3 induces chondrogenesis through the activation of SOX9 via CREB-binding protein/p300 recruitment. J Biol Chem 280(9):8343-50.
23. Gallo V, Bertolotto A. 1990. Extracellular matrix of cultured glial cells: selective expression of chondroitin 4-sulfate by type-2 astrocytes and their progenitors. Exp Cell Res 187(2):211-23.
24. Gotting C, Kuhn J, Zahn R, Brinkmann T, Kleesiek K. 2000. Molecular cloning and expression of human UDP-d-Xylose:proteoglycan core protein beta-d-xylosyltransferase and its first isoform XT-II. J Mol Biol 304(4):517-28.
25. Grimpe B, Silver J. 2004. A novel DNA enzyme reduces glycosaminoglycan chains in the glial scar and allows microtransplanted dorsal root ganglia axons to regenerate beyond lesions in the spinal cord. J Neurosci 24(6):1393-7.
26. Gris P, Murphy S, Jacob J E, Atkinson I, Brown A. 2003. Differential gene expression profiles in embryonic, adult-injured and adult-uninjured rat spinal cords. Mol Cell Neurosci 24(3):555-67.
27. Hammarback J A, McCarthy J B, Palm S L, Furcht L T, Letourneau P C. 1988. Growth cone guidance by substrate-bound laminin pathways is correlated with neuron-to-pathway adhesivity. Dev Biol 126(1):29-39.
28. Hartsough M T, Mulder K M. 1997. Transforming growth factor-beta signaling in epithelial cells. Pharmacol Ther 75(1):21-41.
29. Heldin C H, Westermark B. 1999. Mechanism of action and in vivo role of platelet-derived growth factor. Physiol Rev 79(4):1283-316.
30. Janeczko K. 1988. The proliferative response of astrocytes to injury in neonatal rat brain. A combined immunocytochemical and autoradiographic study. Brain Res 456(2):280-5.
31. Jones L L, Margolis R U, Tuszynski M H. 2003. The chondroitin sulfate proteoglycans neurocan, brevican, phosphacan, and versican are differentially regulated following spinal cord injury. Exp Neurol 182(2):399-411.
32. Kawakami Y, Tsuda M, Takahashi S, Taniguchi N, Esteban C R, Zemmyo M, Furumatsu T, Lotz M, Belmonte J C, Asahara H. 2005. Transcriptional coactivator PGC-1alpha regulates chondrogenesis via association with Sox9. Proc Natl Acad Sci USA 102(7):2414-9
33. Kolb M, Margetts P J, Galt T, Sime P J, Xing Z, Schmidt M, Gauldie J. 2001. Transient transgene expression of decorin in the lung reduces the fibrotic response to bleomycin. Am J Respir Crit Care Med 163(3 Pt 1):770-7.
34. Kordes U, Cheng Y C, Scotting P J. 2005. Sox group E gene expression distinguishes different types and maturational stages of glial cells in developing chick and mouse. Brain Res Dev Brain Res 157(2):209-13.
35. Lagord C, Berry M, Logan A. 2002. Expression of TGF-beta2 but not TGFbeta1 correlates with the deposition of scar tissue in the lesioned spinal cord. Mol Cell Neurosci 20(1):69-92.
36. Lefebvre V, Huang W, Harley V R, Goodfellow P N, de Crombrugghe B. 1997. SOX9 is a potent activator of the chondrocyte-specific enhancer of the pro alpha1(II) collagen gene. Mol Cell Biol 17(4):2336-46.
37. Liesi P, Silver J. 1988. Is astrocyte laminin involved in axon guidance in the mammalian CNS? Dev Biol 130(2):774-85.
38. Logan A, Baird A, Berry M. 1999a. Decorin attenuates gliotic scar formation in the rat cerebral hemisphere. Exp Neurol 159(2):504-10.
39. Logan A, Green J, Hunter A, Jackson R, Berry M. 1999b. Inhibition of glial scarring in the injured rat brain by a recombinant human monoclonal antibody to transforming growth factor-beta2. Eur J Neurosci 11(7):2367-74.
40. Matthiessen H P, Schmalenbach C, Muller H W. 1989. Astroglia-released neurite growth-inducing activity for embryonic hippocampal neurons is associated with laminin bound in a sulfated complex and free fibronectin. Glia 2(3):177-88.
41. McKeon R J, Jurynec M J, Buck C R. 1999. The chondroitin sulfate proteoglycans neurocan and phosphacan are expressed by reactive astrocytes in the chronic CNS glial scar. J Neurosci 19(24):10778-88.
42. McKeon R J, Schreiber R C, Rudge J S, Silver J. 1991. Reduction of neurite outgrowth in a model of glial scarring following CNS injury is correlated with the expression of inhibitory molecules on reactive astrocytes. J Neurosci 11(11):3398-411.
43. Morgenstern D A, Asher R A, Fawcett J W. 2002. Chondroitin sulphate proteoglycans in the CNS injury response. Prog Brain Res 137:313-32.
44. Nakamura M, Okada S, Toyama Y, Okano H. 2005. Role of IL-6 in spinal cord injury in a mouse model. Clin Rev Allergy Immunol 28(3):197-204.
45. Nelander S, Larsson E, Kristiansson E, Mansson R, Nerman O, Sigvardsson M, Mostad P, Lindahl P. 2005. Predictive screening for regulators of conserved functional gene modules (gene batteries) in mammals. BMC Genomics 6(1):68.
46. Neugebauer K M, Tomaselli K J, Lilien J, Reichardt L F. 1988. N-cadherin, NCAM, and integrins promote retinal neurite outgrowth on astrocytes in vitro. J Cell Biol 107(3):1177-87.
47. Okada S, Nakamura M, Mikami Y, Shimazaki T, Mihara M, Ohsugi Y, Iwamoto Y, Yoshizaki K, Kishimoto T, Toyama Y and others. 2004. Blockade of interleukin-6 receptor suppresses reactive astrogliosis and ameliorates functional recovery in experimental spinal cord injury. J Neurosci Res 76(2):265-76.
48. Pasinetti G M, Nichols N R, Tocco G, Morgan T, Laping N, Finch C E. 1993. Transforming growth factor beta 1 and fibronectin messenger RNA in rat brain: responses to injury and cell-type localization. Neuroscience 54(4):893-907.
49. Reier P J, Houle J D. 1988. The glial scar: its bearing on axonal elongation and transplantation approaches to CNS repair. Adv Neurol 47:87-138.
50. Rogers S L, Letourneau P C, Palm S L, McCarthy J, Furcht L T. 1983. Neurite extension by peripheral and central nervous system neurons in response to substratum-bound fibronectin and laminin. Dev Biol 98(1):212-20.
51. Rogers S L, Letourneau P C, Peterson B A, Furcht L T, McCarthy J B. 1987. Selective interaction of peripheral and central nervous system cells with two distinct cell-binding domains of fibronectin. J Cell Biol 105(3):1435-42.
52. Schaeren-Wiemers N, Gerfin-Moser A. 1993. A single protocol to detect transcripts of various types and expression levels in neural tissue and cultured cells: in situ hybridization using digoxigenin-labeled cRNA probes. Histochemistry 100:431-440.
53. Schonherr E, Jarvelainen H T, Sandell L J, Wight T N. 1991. Effects of platelet-derived growth factor and transforming growth factor-beta 1 on the synthesis of a large versican-like chondroitin sulfate proteoglycan by arterial smooth muscle cells. J Biol Chem 266(26):17640-7.
54. Stolt C C, Lommes P, Sock E, Chaboissier M C, Schedl A, Wegner M. 2003. The Sox9 transcription factor determines glial fate choice in the developing spinal cord. Genes Dev 17(13):1677-89.
55. Tom V J, Doller C M, Malouf A T, Silver J. 2004. Astrocyte-associated fibronectin is critical for axonal regeneration in adult white matter. J Neurosci 24(42):9282-90.
56. Tomaselli K J, Neugebauer K M, Bixby J L, Lilien J, Reichardt L F. 1988. N-cadherin and integrins: two receptor systems that mediate neuronal process outgrowth on astrocyte surfaces. Neuron 1(1):33-43.
57. Vijayan V K, Lee Y L, Eng L F. 1990. Increase in glial fibrillary acidic protein following neural trauma. Mol Chem Neuropathol 13(1-2):107-18.
58. Wehrli B M, Huang W, De Crombrugghe B, Ayala A G, Czerniak B. 2003. Sox9, a master regulator of chondrogenesis, distinguishes mesenchymal chondrosarcoma from other small blue round cell tumors. Hum Pathol 34(3):263-9.
59. Wiksten M, Vaananen A J, Liebkind R, Liesi P. 2004. Regeneration of adult rat spinal cord is promoted by the soluble KDI domain of gamma1 laminin. J Neurosci Res 78(3):403-10.
60. Wilson J X, Dixon S J. 1989. Ascorbic acid transport in mouse and rat astrocytes is reversibly inhibited by furosemide, SITS, and DIDS. Neurochem Res 14(12):1169-75.
61. Yamauchi S, Mita S, Matsubara T, Fukuta M, Habuchi H, Kimata K, Habuchi O. 2000. Molecular cloning and expression of chondroitin 4-sulfotransferase. J Biol Chem 275(12):8975-81.
62. Zuo J, Neubauer D, Dyess K, Ferguson T A, Muir D. 1998. Degradation of chondroitin sulfate proteoglycan enhances the neurite-promoting potential of spinal cord tissue. Exp Neurol 154(2):654-62.
63. Fok-Seang, J., L. C. Smith-Thomas, et al. (1995). "An analysis of astrocytic cell lines with different abilities to promote axon growth." *Brain Res* 689(2): 207-23.
64. Gris, P., A. Tighe, et al. (2007). "Transcriptional regulation of scar gene expression in primary astrocytes." *Glia* 55(11): 1145-55.
65. Weston, A. D., R. A. S. Chandraratna, et al. (2002). "Requirement for RAR-mediated gene repression in skeletal progenitor differentiation." *J. Cell Biol.* 158(1): 39-51.

All references are incorporated herein by reference.

We claim:

1. A method of down-regulating the activity of a chondroitin sulfate proteoglycan in a mammal comprising the step of inhibiting SOX9 activity in the mammal, wherein the SOX9 has the amino acid sequence as set out in SEQ ID No: 1, or a functionally equivalent sequence of SOX9, and wherein the SOX9 activity is inhibited using an oligonucleotide or an antibody.

2. The method as defined in claim 1, wherein SOX9 activity is inhibited by an antisense oligonucleotide or siRNA.

3. The method of claim 1, wherein the SOX9 has the amino acid sequence as set out in SEQ ID No: 1, SEQ ID No: 2 or SEQ ID No: 3.

4. The method of claim 3, wherein the SOX9 has the amino acid sequence as set out in SEQ ID No: 1.

5. The method of claim 2, wherein the siRNA targets a gene encoding SOX9.

6. The method of claim 5, wherein the siRNA has the sequence of SEQ ID No: 4.

* * * * *